United States Patent
Le Febre

(12) 
(10) Patent No.: US 6,749,735 B1
(45) Date of Patent: Jun. 15, 2004

(54) ELECTROMOBILITY FOCUSING CONTROLLED CHANNEL ELECTROPHORESIS SYSTEM

(76) Inventor: David Le Febre, P.O. Box 949 4665 Puerta del Sol, Camino, CA (US) 95709

( * ) Notice: Subject to any disclaimer, the term of this patent is extended or adjusted under 35 U.S.C. 154(b) by 0 days.

(21) Appl. No.: 09/526,920

(22) Filed: Mar. 16, 2000

(51) Int. Cl.[7] .................. G01N 27/26; G01N 27/447

(52) U.S. Cl. .................. 204/601; 204/450; 204/451; 204/454; 204/600

(58) Field of Search ................ 204/450, 451, 204/454, 600, 601

(56) References Cited

U.S. PATENT DOCUMENTS

| | | | |
|---|---|---|---|
| 5,092,972 A | 3/1992 | Ghowsi | 204/454 |
| 5,151,164 A | 9/1992 | Blanchard et al. | 204/451 |
| 5,180,475 A | 1/1993 | Young et al. | 204/454 |
| 5,262,031 A | 11/1993 | Lux et al. | 204/601 |
| 5,282,942 A | 2/1994 | Herrick et al. | 204/454 |
| 5,320,730 A | 6/1994 | Ewing et al. | 204/603 |
| 5,441,613 A | 8/1995 | McCormick et al. | 204/452 |
| 5,559,442 A | 9/1996 | Peier et al. | 324/753 |
| 5,728,282 A | 3/1998 | Bashkin et al. | 204/455 |
| 5,800,690 A | 9/1998 | Chow et al. | 204/451 |
| 5,810,985 A | 9/1998 | Bao et al. | |
| 5,882,465 A | 3/1999 | McReynolds | 156/285 |
| 5,900,934 A | 5/1999 | Gilby et al. | 356/344 |
| 5,948,227 A | 9/1999 | Dubrow | 204/455 |
| 5,955,028 A | 9/1999 | Chow | 422/63 |
| 5,957,579 A | 9/1999 | Kopf-Sill et al. | 366/340 |
| 5,958,202 A | 9/1999 | Regnier et al. | 204/451 |
| 5,958,203 A | 9/1999 | Parce et al. | 204/451 |
| 5,958,694 A | 9/1999 | Nikiforov | 435/6 |
| 5,959,291 A | 9/1999 | Jensen | 250/214 R |
| 5,964,995 A | 10/1999 | Nikiforov et al. | 204/450 |
| 5,965,001 A | 10/1999 | Chow et al. | 204/600 |
| 5,965,410 A | 10/1999 | Chow et al. | 435/91.2 |
| 5,972,187 A | 10/1999 | Parce et al. | 204/453 |
| 5,976,336 A | 11/1999 | Dubrow et al. | 204/453 |
| 5,989,402 A | 11/1999 | Chow et al. | 204/601 |
| 6,001,229 A | 12/1999 | Ramsey | 204/451 |
| 6,010,608 A | 1/2000 | Ramsey | 204/453 |
| 6,277,258 B1 * | 8/2001 | Ivory et al. | 204/450 |

OTHER PUBLICATIONS

Journal of Chromatography A, 229 (1996) 229–236 "Focusing Proteins in an Electric Field Gradient", Wendy S. Koegler and Cornelius F. Ivory.

Anal. Chem., 199, 71, 1628–1632, "Digitally Controlled Electrophoretic Focusing", Zheng Huang and Cornelius F. Ivory.

Biotechnol. Prog. 1998, 14, 300–309, "Protein Focusing In a Conductivity Gradient", Robert D. Greenlee and Cornelius F. Ivory.

Ann. Rev. Biophys. Bkiophys. Chem 1998, 17:287–304, "Pulsed–Field Gel Electrophoresis of Very Large DNA Molecules", Charles R. Cantor, Cassandra L. Smith and Matthew K. Mathew.

(List continued on next page.)

Primary Examiner—Nam Nguyen
Assistant Examiner—John S Starsiak
(74) Attorney, Agent, or Firm—Thorpe North & Western L.L.P.

(57) ABSTRACT

An electromobility focusing controlled channel electrophoresis system includes a first separation channel including an electric field intensity gradient profile in which the intensity is a continuous function of position within the channel over at least a portion of the channel, and the electrophoretic migration facilitated by the electric field is countered by an opposing force, which can be an electroosmotic flow force, to focus analyte species in the separation channel. A second channel including an analyte concentrator and a collection or transfer port is fluidly connected to the first channel by a steering valve facilitating manipulation of separated analyte species. Means for altering and controlling the electroosmotic force for moving analytes within the system and detectors configured for detecting analyte species are also included.

61 Claims, 10 Drawing Sheets

OTHER PUBLICATIONS

J. Am. Chem. Soc., 1996, 68, 3441–3449, "Flow Injection Analysis Using Continuous Channel Electrophoresis", J. M. Mesaros, P. F. Gavin and A. G. Ewing.

Journal of Chromatrography A., 676 (1994), 409–420, "New Approaches to Concentration on a Microliter Scale of Dilute Samples, Particularly Biopolymers With Special Reference to Analysis of Peptides and Proteins by Capillary Electrophoresis", Stellan Hjerten, Jia–Li Liao and Rong Zhan.

Anal. Chem., 1993, 65, 3313–3319, "Continuous Electrophoretic Separations in Narrow Channels Coupled to Small–Bore Capillaries", J. M. Mesaros, G. Luo, J. Roeraade and a. G. Ewing.

Anal. Chem. 1992, 64, 2348–2351, "Enhanced Separation of DNA Restriction Fragments by Capillary Gel Electrophoresis Using Field Strength Gradients", Andras Guttman, Bart Wanders and Nelson Cooke.

Anal. Chem. 1991, 63, 2795–2797, "Improved Separation of Mucleic Acids With Analyte Velocity Modulation Capillary Electrophoresis", Tshenge Demana, Maureen Lanan and Michael D. Morris.

Biotechnol. Prog. 1990, 6, 21–32, "Continuous Counteracting Chromatographic Electrophoresis", Cornelius F. Ivory and William A. Gobie.

Counteracting Chromatographic Electrophesis, 18(1), 1–64 (1989), "A Theoretical and Experimental Study of Counteracting Chromatographic Electrophoresis", Bruce R. Locke and Ruben G. Carbonell.

Counteracting Chromatographic Electrophesis, 18(1), 54–109 (1989), "A Theoretical and Experimental Study of Use of Electric Fields in Solvent Extraction: A Review and Prospectus", Timothy C. Scott.

Journal of Biochemical and Biophysical Methods, "Field Gradients Improve Resolution on DNA Sequencing Gels", W. ansorge and S. Labeit.

Proc. Natl. Aca. Sci. USA, vol. 80 pp. 3963–3965, Jul. 1983, "Buffer Gradient Gels and S Label as an Aid to Rapid DNA Sequence Determination", M. D. Biggin, T. J. Gibson and G .F. Hong.

Analytical Biochemistry 120, 12–18, 1982, "Nonuniform Field Gel Electrophoresis", C. Dennison, W. A. Lindner and N. C. K. Phillips.

Science, vol. 227, "Separation Techniques Based on the Opposition of Two Cunteracting Forces to Produce a Dynamic Equilibrium", Patrick H. O'Farrell.

* cited by examiner

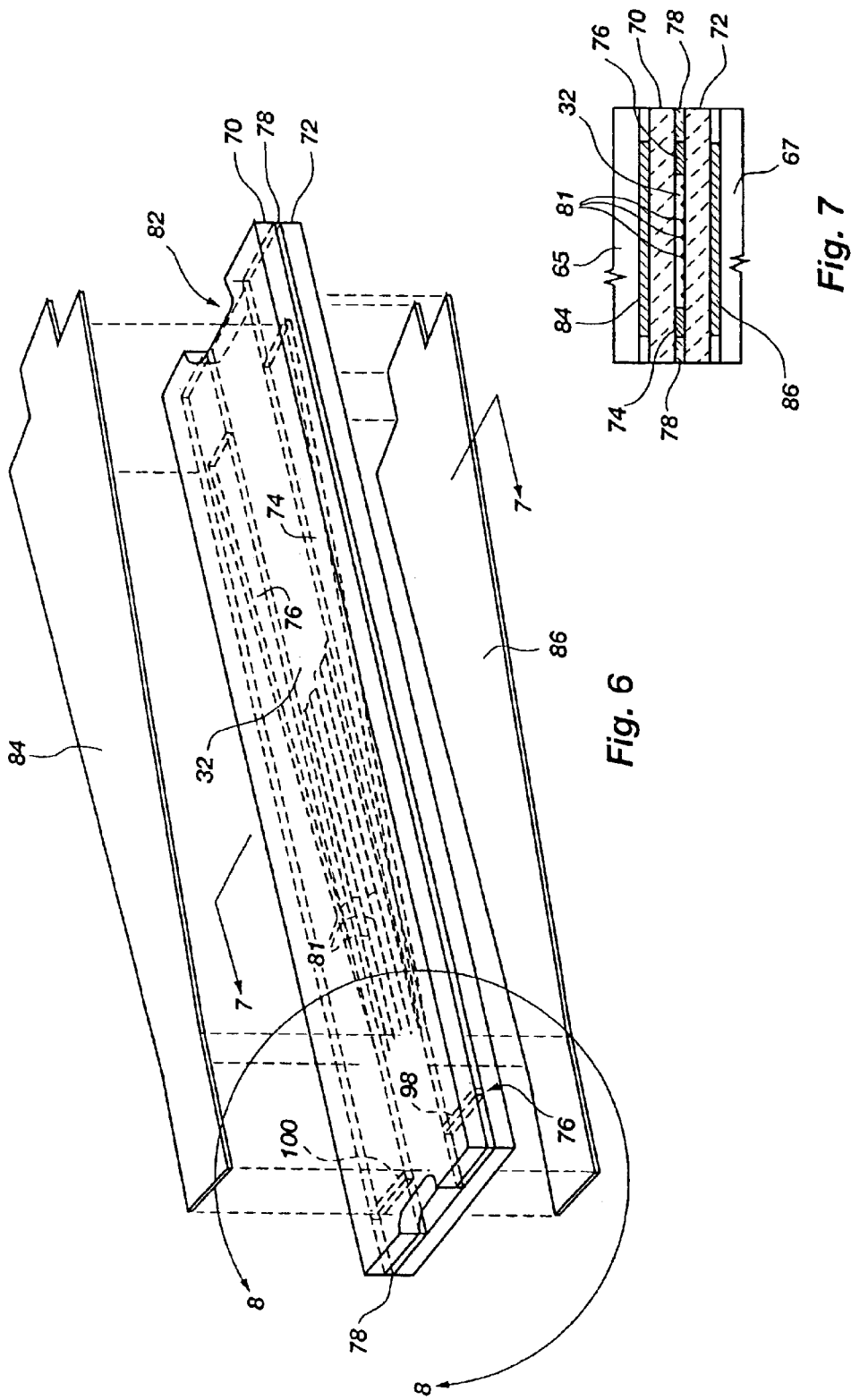

ELECTROMOBILITY FOCUSING CONTROLLED CHANNEL ELECTROPHORESIS SYSTEM

BACKGROUND

1. Field of the Invention

The invention relates to analytical procedures for investigating analyte species in a fluid sample. More specifically, the invention relates to methods and apparatus for separation and manipulation of analytes, and their application in diagnostic qualitative and quantitative procedures.

2. Brief Description of Related Art

Electrormigration separation processes, such as capillary zone electrophoresis and micellular electrokinetic capillary chromatography and other similar processes, are known and are widely used. For example, these processes are used in research and in various testing applications such as separations of proteins and DNA fragments. Control, and particularly fine control, of these processes is an-area of ongoing research and development efforts, as manipulation of quantities of analyte species for separation and qualitative and quantitative analysis is recognized as a significant technical challenge, but one potentially yielding great benefits in scientific endeavors and applications in areas such as healthcare that could potentially greatly benefit humankind.

Taking as an example capillary electrophoresis (CE), and with reference to FIG. 1 which is a generalized schematic diagram of CE, a capillary tube 12 having a longitudinal axis is disposed between two fluid wells positioned at its ends. An electrolyte solution, such as a buffer solution, is contained in the wells and an interior channel defined by the capillary. A cathode 14 is positioned in fluid communication with the electrolyte solution at one end and the anode 16 at the other. An applied voltage potential across the cathode and anode gives the potential or voltage profile 20 shown in the diagram. This is a straight line having a slope equal to the magnitude of the potential difference over the length of the channel. The electric field 22 created in the capillary is a constant throughout its length as shown. This of course is because the channel is of uniform cross-section and the voltage drop per unit of distance along the longitudinal axis of the channel is a constant value. In other words, the derivative of the function defined by the voltage as a function of position along the axis is a constant and, accordingly, the field generated is also of a constant intensity along the longitudinal axis.

Moreover, as is known in electrophoretic processes, an electrolyte solution, which provides a medium in which analytes to be investigated, e.g. separated and identified, are resident during separation, can be subject to electroosmotic flow, and such flow in small channels is a plug or bulk flow. Further, it has been recognized that electroosmotic bulk flow of electrolyte fluid in electrophoretic processes can be used to enhance separation, and also to do other things, such as to move analytes around within a electrophoretic separation apparatus. For example, U.S. Pat. No. 5,151,164, U.S. Pat. No. 5,180,475 and U.S. Pat. No. 5,320,730 disclose methods and apparatus for controlling the electroosmotic bulk flow of electrolyte solutions in electrophoretic processes, and the disclosures of these patents are hereby incorporated herein by reference.

It is known that control of the polarity and magnitude of charge accumulation adjacent to the inner surface of containments (such as fused silica capillary tubes) wherein the electrolyte solution dwells during electrophoretic separations (known in the art as the zeta potential) effectively controls electroosmotic bulk flow in small channels. This has been explained in terms of viscous coupling of molecules in solution with accumulations of charged molecules adjacent to the inner surface, such accumulated charged molecules being actuated in a longitudinal direction toward a cathode or anode (depending on polarity) by the electric field within the containment. As mentioned, this effect has been found to create a reproducible "plug" flow of electrolyte solution, and that this flow is relatively stable. Thus, in electrophoretic separation processes, analytes may be carried along in the bulk flow of the electrolyte solution, which fact can be used to move analytes, and assist in the separation of distinct analyte species based on differing mobilities of constituent molecules in the electrolyte solution (and any other media, such as a gel, which also may be present) within the separation channel.

For example, it is known that resolution of discrete analyte species having similar mobilities is enhanced by balancing electroosmotic flow against electrophoretic migration. Depending on whether cations or anions are of interest, the polarity and magnitude of the zeta potential is selected by applying an appropriate potential at the outer surface of a capillary having appropriate dielectric properties. Applying sufficient external potential of the same polarity as the molecules collecting at the surface overcomes the electroosmotic flow regime spontaneously occurring in the direction of electrophoretic migration by reversing the polarity of the inner surface, causing the spontaneously accumulating molecules to disperse and those of opposite polarity to migrate to the inner surface, setting up bulk flow in the opposite direction. As will be recognized, by application of appropriate potential external to the capillary, the electroosmotic flow within it can be increased, decreased, stopped and reversed.

However, manipulation of the electromagnetic forces effecting electrophoretic migration of charged species, which gives rise to separation, is less well recognized and understood as a tool in enhancing separation. Some work in this area has been done. For example, two published articles discuss localized modification of the intensity of the electric field for the purpose of improving resolution of analyte species. In an article [Kroegler and Ivory] published in [Journal of Chromatography A, 229 (1996) 229–236] there is a disclosure of a separation system wherein an electric field intensity which varies as a function of position, providing a sloping intensity profile along a longitudinal axis of the apparatus, is balanced against a pump-induced flow providing a counter-acting force. However, the system disclosed requires two flow fields, separated by a length of dialysis membrane tubing. One field comprises an electrolyte solution in which the electric field is propagated and is bounded by a trumpet shaped containment. The flared shape of the containment provides a cross section which varies as a non-linear continuous function of position along a longitudinal axis, and therefore gives an electric field within the channel that varies in intensity as a continuous function of position. Ions can cross the membrane, and the field extends within the other flow regime, but analyte molecules cannot pass out of the membrane into the electrolyte solution outside it. A buffer solution containing the analyte sample to be separated is pumped through the tubing in a direction opposite to the electrophoretic migration of the molecules of interest, and differences in electrophoretic mobility causes analyte species to "focus" at differing equilibrium points where the electrophoretic force balances the bulk flow force for each molecule of a species. In other words the molecules will stop at different points corresponding to balanced forces acting on them, and like molecules will stop at like points along the longitudinal axis.

In the other published reference [Huang and Ivory] [Anal. Chem. 1999, 71, 1628–1632], the electric field intensity is altered locally by 50 electrodes spaced along the longitudinal axis of the apparatus. A potential is applied at each electrode, the result taught being to provide a gradient in intensity. Like the previous article, the analyte of interest is contained in a flow regime separated from a second flow regime by dialysis tubing. The tubing is packed with gel which provides an opposition to flow of fluids and to electrophoretic migration though the tubing. A bulk flow in opposition to electrophoretic migration is taught, with a focusing effect similar to that discussed above. However, the electric field intensity appears to:be a stair-step function of position (49 equilibrium positions) with discontinuities where the width of the electrodes create small zones of constant electric potential. As can be seen in FIG. 2, which is a schematic representation of at least a portion of the apparatus described in the reference, the potential (voltage) profile 20 is a construct of segments having differing slopes depending upon the voltages applied at each electrode 24 of the 50 electrode array. The electric field intensity profile 22 appears to be a distribution of "plateaus" forming the tread portion of the stair step function, the height of each correlating with the slope of the voltage profile at the same location along the longitudinal axis 26 of the channel 28. The intensity (magnitude) of the electric field being constant between electrodes, there is no counter, or "restoring" force regime between electrodes tending to focus differing analyte species of slightly differing mobilities to differing locations on the "plateau" or stair step of constant field intensity over the space between adjacent electrodes. Therefore, it appears that unless the potential differences between electrodes are sufficiently small, individual analyte species cannot be separated. If numerous analyte species are present in the sample and the differences in mobilities are both small and large, multiple runs will be required.

At least some difficulties appear to be inherent in the two approaches disclosed in the journal references mentioned above, the first being a need to provide a separate flowpath for the analytes and buffer, as distinguished from other fluid media within a separation apparatus (in both cases separated by a membrane tubing), which other fluid media acts as a coolant in addition to propagating the electric field. Another is the stair step function of electric field intensity mentioned does not allow separation of more analyte species than the number of electrodes provided; and two or more of similar mobility could be indistinguishably mixed at the location of a single stair "step."

SUMMARY OF THE INVENTION

It has been recognized that the effectiveness of separation and the isolation of individual analyte species for identification can be enhanced by enabling more precise control over separation processes. The addition of other tools for manipulation of analyte species to a separation system has also been recognized as desirable to enable an electrophoretic separation system to perform tasks previously not undertaken in detection and analysis of disease states, and other analytical endeavors. One attribute of a separation system recognized as very desirable is to separate a sample containing hundreds if not thousands of analyte species, many of which have mobilities which are very similar, in a single separation run in a single channel.

The system of the invention accordingly provides an electromobility focusing system, which in a broad sense is defined herein as a system for separation and/or concentration of individual analyte species according to their electrophoretic mobilities in a medium, and in a more detailed aspect comprising a liquid-phase controlled channel electrophoresis separation system configured to separate at least one discrete analyte species from an analyte sample comprising:

1) a separation channel defined by a confinement enclosing an interior channel volume, said separation channel having first and second ends and a longitudinal axis, and said separation channel-being configured to contain an electrolyte solution within the interior channel volume, wherein the separation channel provides the only flowpath for both the analyte sample and the electrolyte solution;

2) a continuous electric field intensity gradient generator configured to apply a electric field intensity gradient within the separation channel along the longitudinal axis over at least a portion of the separation channel intermediate the first and second ends, the intensity of electric field generated varying as a continuous function of location along the longitudinal-axis, whereby electrophoretic migration of an analyte species within the separation channel is actuated by a force that varies with position along the longitudinal axis as a continuous function of position along the longitudinal axis within said portion of the separation channel;

3) an electroosmotic flow generator configured to generate an electroosmotic flow along thee longitudinal axis of the separation channel, which electroosmotic flow is variable as to at least one of: (i) the magnitude of the flow, and (ii) the direction of the flow, to enhance separation of said at least one analyte species by enabling control of an interaction of forces acting on it created by the continuous electric field tensity gradient generator and the electroosmotic flow generator.

In a more detailed aspect, such a system can be provided wherein the electroosmotic flow generator comprises a power supply and a distributed source of potential positioned adjacent said containment on an exterior surface. As a result, the zeta potential of an interior surface in fluid contact with the separation channel can be altered by at least one of: a) applying a potential, and b) altering at least one of: (i) the magnitude, and (ii) polarity, of potential applied, to the distributed source of potential from the power supply.

In a further more detailed aspect, the continuous electric field intensity gradient generator can further comprise: 1) a cathode positioned adjacent one of the first and second ends of the separation channel; 2) an anode positioned adjacent the other of the first and second ends of the separation channel; 3) a power supply in electric communication with the cathode and the anode; 4) a continuously varying resistor, which can be a contour resistor in fluid communication with the separation channel along at least a portion of the longitudinal axis intermediate the first and second ends, said resistor having a resistance that varies as a continuous function of position along the longitudinal axis of the separation channel, whereby an electric potential in the electrolyte fluid varies a non-linear continuous function of position along the longitudinal axis of the separation channel, and as a result the electric field intensity varies as a continuous functions of position along the longitudinal axis over at least a portion of the separation channel intermediate the first and second ends.

A continuously varying resistor in fluid communication with the separation channel along at least a portion of the longitudinal axis intermediate the first and second ends comprises a resistor having a resistance that varies as a continuous function of position along the longitudinal axis of the separation channel, whereby an electric potential in the electrolyte fluid varies as a non-linear continuous function of position along the longitudinal axis of the separation channel, and as a result the electric field intensity varies as a continuous function of position along the longitudinal axis over at least a portion of the separation channel intermediate the first and second ends. Such a resistor can comprise a contour resistor which contacts the fluid within the channel by forming a part of the channel wall, or the continuously varying resistor can comprise a filament within the separation channel, or the continuously varying resistor can comprise some other variable, such as a packing within the separation channel that varies in resistivity as a continuous function of position along the longitudinal axis. In further detail, a contour resistor can comprise a conductive material having a cross sectional shape which varies as a continuous function of position along the longitudinal axis. Alternatively, the contour resistor can be configured so that it has a material property that varies as a continuous function of position along said longitudinal axis.

In another more detailed aspect, a fluid electrolyte solution can be disposed in the separation channel, and the electrolyte solution can comprise a buffer solution. The system can further comprise a micellular dispersion or gel disposed in the separation channel. Alternatively the system can comprise a polymeric solution disposed in the separation channel.

In further detail, the containment can be configured to provide a high aspect, substantially rectangular cross-sectional shape for the separation channel. The electroosmotic flow generator can comprise a first plate disposed adjacent one side of the containment and be configured to alter the zeta potential on an interior surface of the separation channel adjacent the first side of the containment, and a second plate adjacent a second side of the containment configured to alter the zeta potential on an interior surface of the containment adjacent the second side of the containment. Said first and second plates can comprise distributed resistors laid down by a screening mask, or other deposition technique.

In another detailed aspect, the system can further comprise a first orientation electric field generator. The first orientation electric field generator can comprise an electroosmotic flow generator as set forth above, wherein the first plate and the second plate are brought to different potentials so as to create a transverse or alignment electric field configured to align bipolar molecules in directions normal to the first and second plates. The orientation electric field can be made to oscillate at a selected frequency. The system can further comprise a second orientation electric field generator configured for generating a second orientation electric field acting in a direction normal to the first orientation electric field, wherein the first and second orientation electric fields can be varied to orient bipolar molecules to a selected orientation by cooperation between the first and second orientation alignment electric fields.

In a further detailed aspects, the system can further comprise: i) a detector configured for detecting analyte species in said separation channel, said detector being positioned intermediate the first and second ends of said separation channel; ii) a steering valve in fluid communication with the separation channel, said steering valve comprising a connecting channel and configured to selectively divert fluid containing analyte species from said separation channel at a location intermediate the first and second ends of the separation channel into the connecting channel, and a second separation channel adapted for containing electrolyte fluid and analyte species, said second separation channel having a longitudinal axis and a first end and a second end, said second separation channel being in fluid communication with the connecting channel of said steering valve at a location intermediate said first and second ends, said second separation channel further comprising a second electric field generator configured for moving analyte species along the second separation channel by at least one of electrophoretic migration and electroosmotic flow; ii) an analyte concentrator located in said second-separation channel intermediate the first and second ends.

In a further detailed aspect the analyte concentrator can comprise a line source of electropotential and an isolated ground, whereby an electric field generated by the second electric field generator can be locally altered so as to focus an analyte species at a location intermediate the first and second ends of the second separation channel. The analyte concentrator can further comprise a first electrode positioned at a first point along the longitudinal axis of the second separation channel, said first electrode being connected to said isolated ground, and a second electrode positioned at a second point along said longitudinal axis of the second separation channel, said second electrode being connected to a source of potential, said source of electropotential being also connected to the isolated ground. The analyte concentrator can further comprise an analyte species detector positioned intermediate said first electrode and said second electrode.

Further features and advantages will be appreciated from the following detailed description, taken in conjunction with the accompanying drawings, which illustrate, by way of example, the features of the invention.

BRIEF DESCRIPTION OF THE DRAWINGS

FIG. 6 is a perspective schematic diagram illustrating a separation portion of the system shown in FIG. 3;

FIG. 7 is a crossectional view, taken along line 7—7 in FIG. 6 of the separation portion shown in FIG. 6;

DESCRIPTION OF THE PRESENTLY PREFERRED EMBODIMENT(S)

Figure 3:
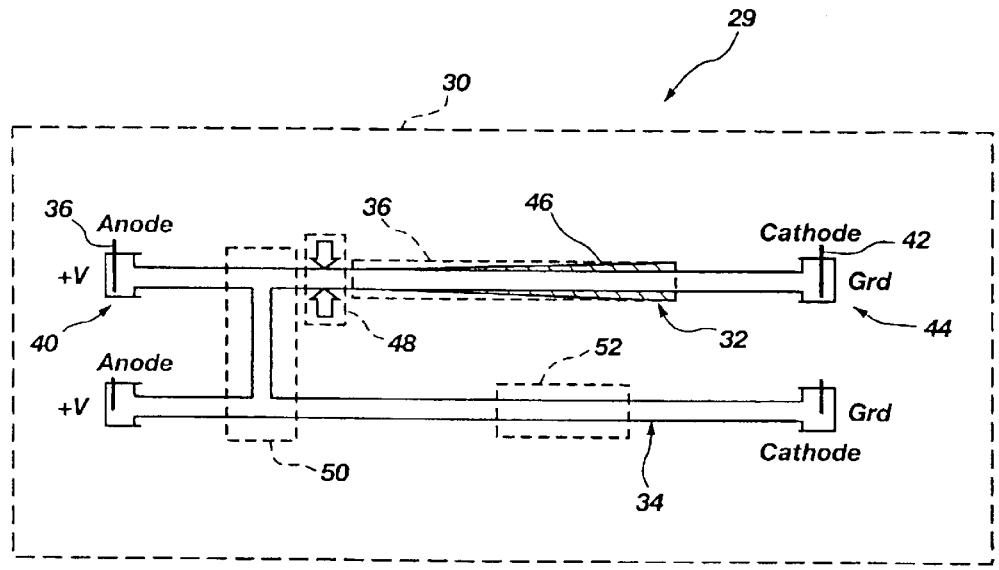
FIG. 3 is a schematic diagram of an electromobility focusing system in accordance with principles of the invention.

With reference to FIG. 3 of the drawings, which are given by way of example, and not by way of limitation, an electromobility focusing system is embodied in a controlled channel electrophoresis system 29, which comprises in one embodiment a monolith 30 with a first, or primary, separation channel 32 and a second (secondary) channel 34 that are interconnected. It will be appreciated from the discussion below that the system can comprise in one, embodiment only a primary channel, and, moreover, that other variations are possible. A system incorporating several elements and a description of their relationship and function as an example of possible embodiment(s) of the invention will illustrate operative principles. A broad overview will be given, and then individual portions of the system and further details of structure and operation will be described in more detail. The primary channel performs analyte species separation using a continuous electric field intensity gradient (CEFIG) and a superimposed electroosmotic force (EOF) along at least a separation portion 36 of the first channel. An anode 36, at a first end 40 of the first channel and a cathode 42 at the second end 44 in combination with a contour resistor 46 enable the CEFIG. Control surfaces regulate the EOF. The electric field intensity gradient in combination with the EOF separates analyte sample, for example a single polarity protein mixture along the length of the longitudinal axis of the channel comprising the separation portion having a CEFIG based on the charge, mass and shape of the individual proteins. The EOF is applied opposite to the direction of migration of the proteins, which results in two separate, but opposite forces being applied to the proteins. These forces drive a given protein to a specific longitudinal channel location. Other proteins with different charges, shapes and masses are driven to other locations along the channel. Thus, a physical separation takes between different mobility proteins along the longitudinal length of the channel. For simplicity of illustration, separation of proteins in a body fluid sample such as blood, urine, spinal fluid, etc., will be discussed, but this is only an example of an analyte sample having analyte species to be separated and detected or investigated, and it will be understood that the invention is not limited to such an exemplary sample application.

Once the proteins or other analyte species have established longitudinal equilibrium along the length of the electric field intensity gradient continuum in the separation portion 36 in the primary channel 32, the EOF is increased incrementally. This results in the lowest mobility proteins nearest the high intensity end of the gradient to move into the constant electric field intensity portion of the primary channel. There the protein fluid segment (containing proteins with the same mobility) is detected by a first or primary detector 48 and routed, by means of a steering valve 50 to the secondary channel. EOF within the secondary channel is also controlled, and is programed to drive the protein segment into an analyte concentrator 52. Depending on the number of protein molecules within the segment and the size of the segment, the analyte concentrator will focus the proteins within a minimum volume fluid segment (by compressing the protein segment together). This segment is then directed into the input port of a analyte identification instrument such as a time-of-flight mass spectrometer (not shown), or to a fraction collector (not shown). In other words, the function of the steering valve is to selectively direct analytes to the concentrator. The function of the concentrator is to enhance and focus the analyte species to improve their subsequent analysis, e.g. identification and quantification. The functions mentioned in the foregoing discussion are carried out under precise monitoring and control. Use of a control system such as an appropriately programmed computer system and appropriate analog to digital, and digital to analog, converters and other interface devices as required (not shown) enables such control.

Figure 1:
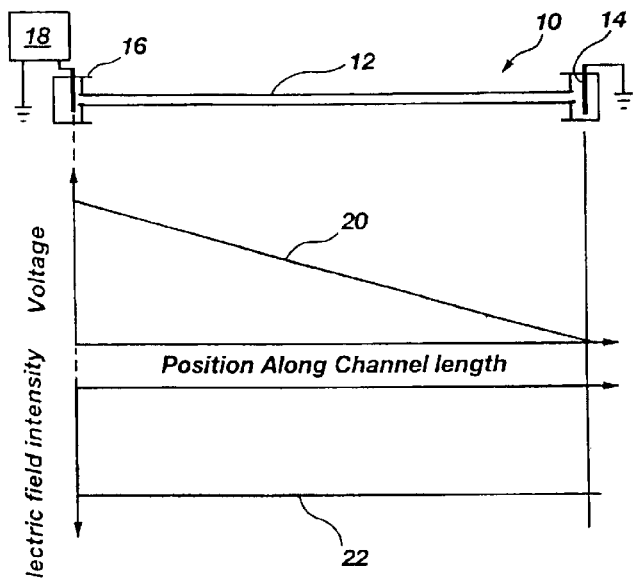
FIG. 1 is a diagram illustrating principles of operation of a prior art CE system.
Figure 2:
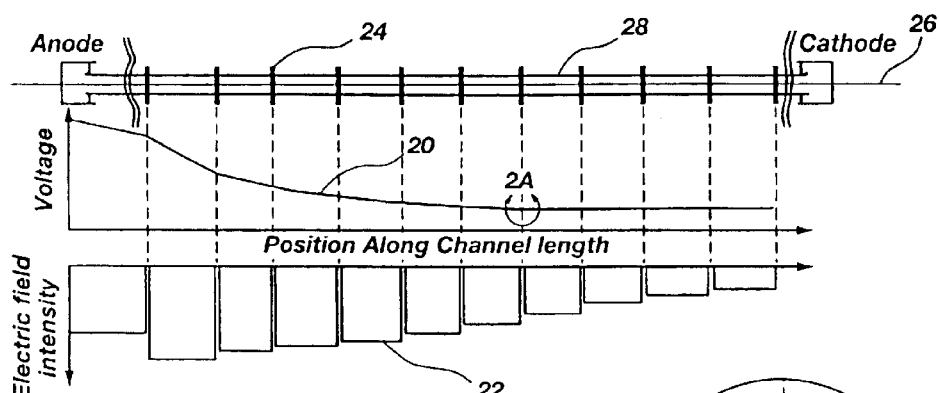
FIG. 2 is a diagram illustrating principles of operation of another prior art separation system.
Figure 2A:
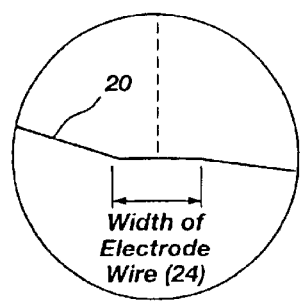
Figure 4:
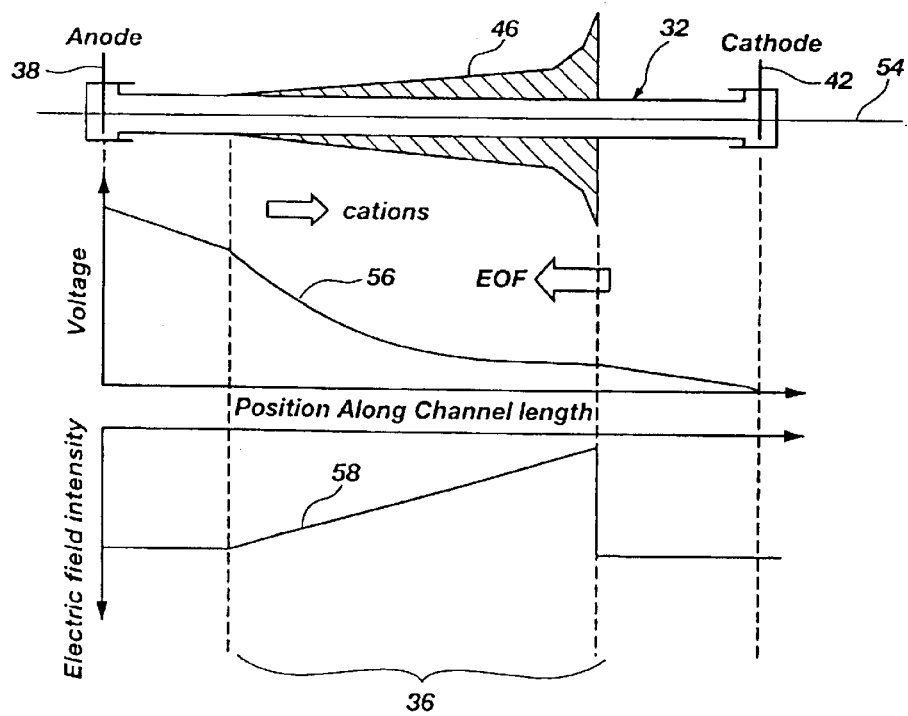
FIG. 4 is a diagram illustrating principles of operation of a portion of the system illustrated in FIG. 3.

Turning now to the diagram shown in FIG. 4, the interrelationship of structure of an exemplary embodiment of the invention and voltage and electric field intensity is illustrated. At this point in the description, it is deemed possibly beneficial to further clarify some terms that have been used in the above description. CEFIG is an electric field intensity gradient continuum. By definition, electric field intensity is the vector force on a unit positive test charge, with units such as newtons per coulomb, or force per unit charge, or volts per meter, and is potential energy. Gradient refers to a change in the electric field intensity with channel length and "continuous" or let "continuum" means that the electric field intensity gradient is continuously changing over the length of the channel but in a uniform way, i.e. there are no discontinuities. The electric field intensity gradient continuum differs from the electric field intensity encountered in conventional capillary electrophoresis as outlined above (and illustrated by FIG. 1) in that capillary electrophoresis has constant electric field intensity along its length.

Again with reference to FIG. 4, in the first channel 32 of the present invention a separation portion 36 includes a contour resistor 46 having a resistance that varies with position along a longitudinal axis 54. Resistance as a function of position is a continuous function. A voltage profile 56 along the length of the channel axis deviates from a straight line in the separation portion due to the variable resistance along the axis facilitated by shunting of current by the contour resistor. As will be appreciated, the wedge shape of the resistor is only an example. Other ways of providing a variable resistance will be apparent to one skilled in the art, for example variation of the inherent resistivity by variation of material(s) such as by variation of percent content of two materials having differing resistivities as a function of position. Also, a simple resistor geometry such as that shown is likely an oversimplification, as lateral current path considerations, and other considerations, tend to alter the idealized voltage profile shown. However, for purposes of this discussion we assume the voltage profile and observe that the resulting electric field intensity profile 58, the derivative of the function comprising the voltage profile, is a sloping continuous function of position along the channel axis in the separation portion 36.

The term EOF in the diagram refers to electroosmotic flow within the channel and acts as an opposing force to achieve protein equilibrium. The EOF is capable of being programmed in both polarity and magnitude by a control surface as will be described in more detail below. Cations travel right in the diagram (toward the cathode 42) and it is believed that proteins of interest are cations. However, as can be appreciated, if anions are of interest, polarity is reversed and the system will separate anions in the same manner.

Figure 5:
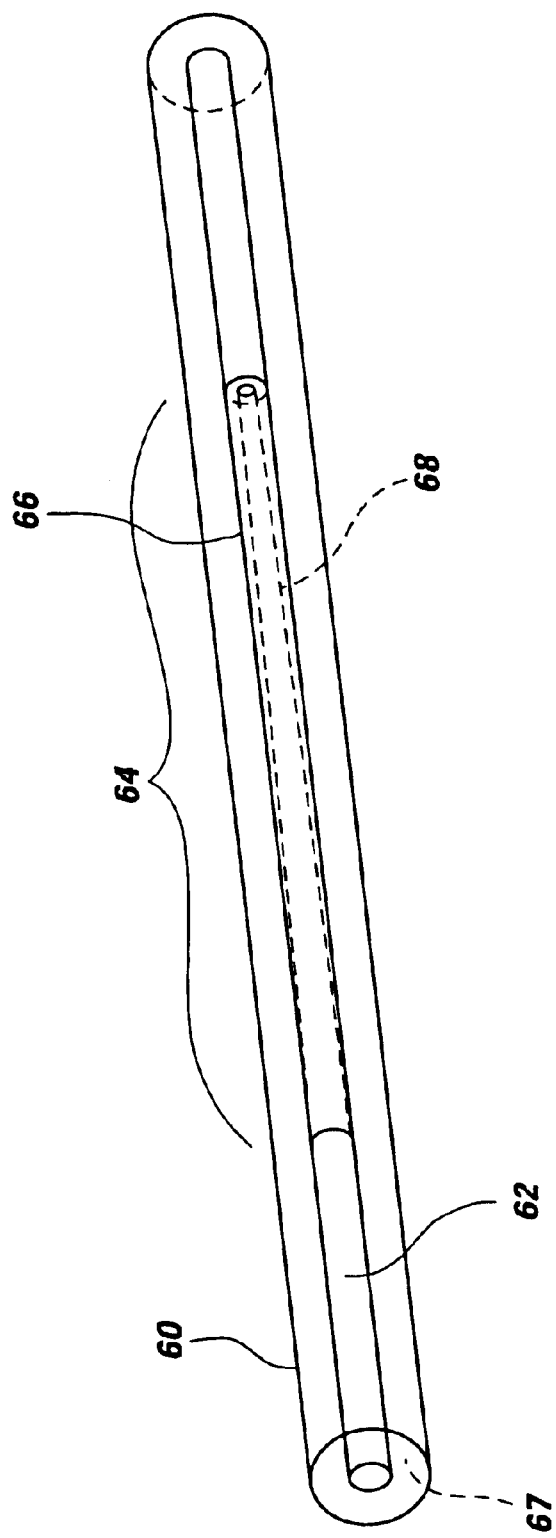
FIG. 5 is a schematic illustration of another embodiment of a portion of the system shown in FIG. 3.

The diagram indicates a channel 32 with contour resistors comprising a wedge-shaped resistive material arranged along each of two opposing sides. While this general configuration is currently preferred, with reference to FIG. 5, it will be appreciated that the functionality discussed can be achieved in other ways. For example in a channel 60 of circular cross section a filament 62 of non-conductive material can be disposed within, and comprise a section 64 comprising a shunt resistor in fluid contact with the interior of the channel and having a variable resistance which is a continuous function of position along the longitudinal axis of the channel. This can be done for example by variation of material 66 deposited on the filament, or varying the diameter of the filament in the shunt resistor segment to form a reduced diameter section 68 as well as varying the thickness of deposited material, or the continuously varying resistor can comprise some other variable, such as a packing within the separation channel 67 that varies in resistivity as a continuous function of position along the longitudinal axis. Other ways of varying the resistance within a segment of a channel of round, rectilinear, or other crossectional shape are possible.

Figure 8:
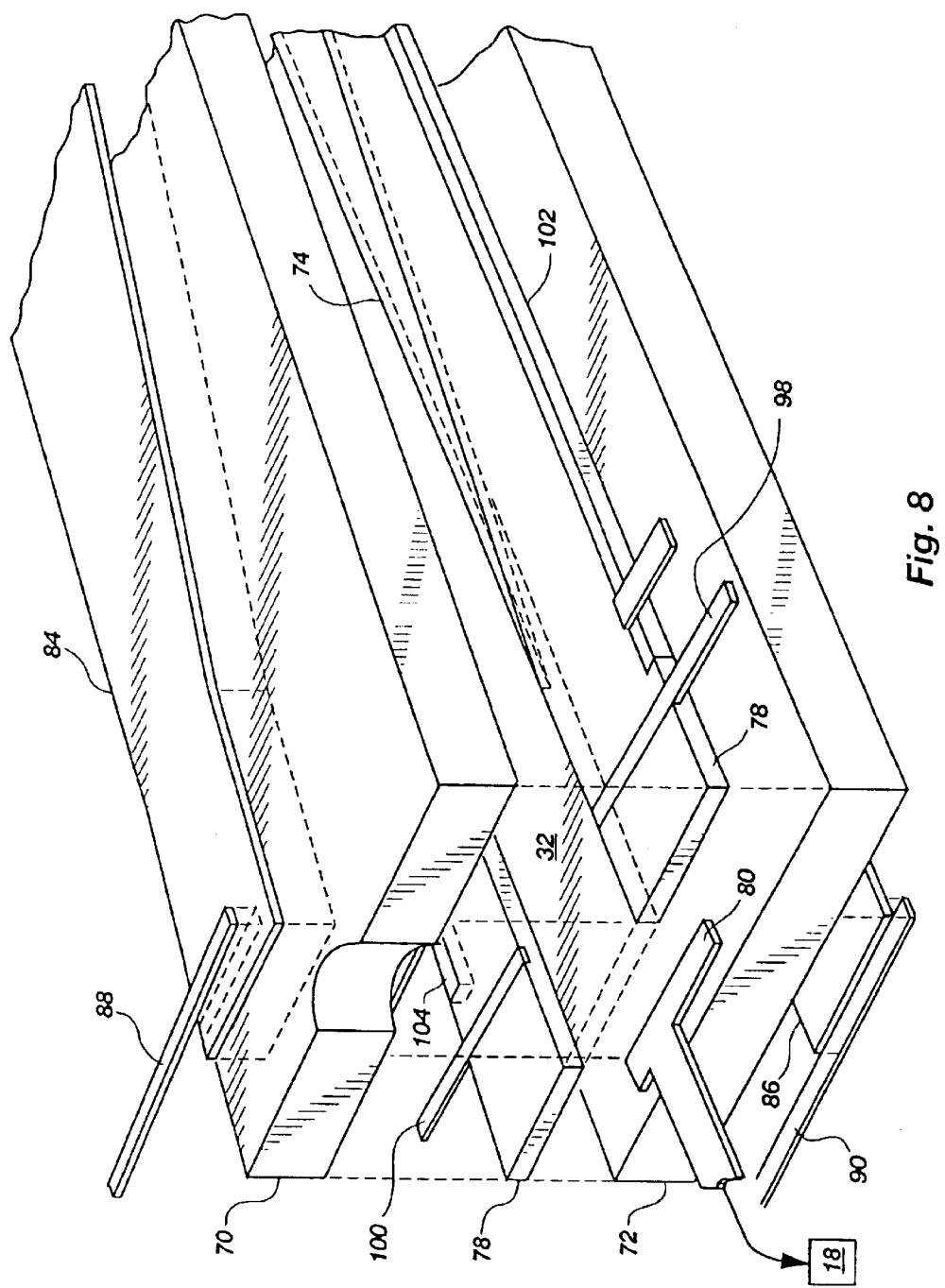
FIG. 8 is an enlarged view, taken at line 8—8 in FIG. 6, of a portion of the separation portion shown in FIG. 6.

With reference to FIGS. 6, 7 and 8, the defining structure and operation of the first, or primary separation channel 32 will now be discussed. It will be understood that the structure will be disposed within and carried by a monolith (not shown) comprising upper 65 and lower 67 plates formed of glass or refractory material having good electrical isolation properties, and outside of these plates a non-conductive coolant fluid flowpath (not shown) is provided to allow a non-conductive coolant to flow past the plates and carry away heat generated by the apparatus to be described. Other connections, conduits, supporting structure, as required to bring in and convey out electrical power and signals indicative of analyte parameters, coolant, optical isolators for electrical power and signals as required, and other structure(s) as will be required, are assumed to be familiar and their necessity and possible configurations apparent to those skilled in the art. In addition to the first channel, the second channel and a connecting channel, a part of the steering valve that connects the primary channel to the secondary channel, are also included in the monolith. The monolith also must provide an interface to a fraction collector, and/or specific detector (e.g. time-of-flight mass spectrometer), from the secondary channel. This monolith structure comprises the foregoing housed in a monolithic laminated ceramic slab measuring in one embodiment about 23 cm×6.0 cm×0.64 cm. This monolith structure comprises the foregoing housed in a monolithic laminated ceramic slab measuring in one embodiment about 23 cm×6.6 cm×6.4 cm.

Signal interfaces for signals both to and from the monolith will comprise isolation means, for example isolation amplifiers (not shown) such as model ISO-106 manufactured by. Burr Brown Inc. of Tucson, Ariz. having a peak DC isolation voltage of approximately 5000 volts. Alternatively, optical isolators of the type typically used to transmit digital signals over high voltage interfaces can be used, or optical waveguide isolation can be used for digital signals.

The upper and lower plates 65, 67 in one embodiment comprise substrates for deposition of layers forming structure therebetween in the finished monolith, such deposition being by screen printing or other mask techniques. Upper and lower substrates with deposited layers are then brought together with proper registration to form the structure described herein, the interface between upper and lower structures being located at a top or bottom surface or within a vertical extent (height dimension) of the channel 32. The plates 65, 67 can be formed in a number of ways, for example they may formed of alumina, or a glass ceramic such as MACOR manufactured by Corning Glass Corporation of Corning N.Y. Forming the plates of widely commercially available KOVAR metal and covering them with a layer of ceramic material is another option. The plates can also be made of boron nitride with an overlay of a ceramic binder suitable to facilitate bonding of thick film inks such as are used to form other layers described below by printing techniques. MULLITE, manufactured by Coors, Inc. of Golden Colo. is a suitable substrate material or an alternate overlay material for boron nitride. The plates comprising substrates and the deposited materials (inks) of the layered structure formed by printing processes should have similar coefficients of thermal expansion and upper temperature limits. The substrate plate material, in addition to being a good electrical insulator, preferably will be a good thermal conductor as heat generated by the monolith will need to be transferred out through the plates 65, 67.

As an alternative to deposition techniques such as screen printing, at least some layers of the monolith can be formed by separate casting. Such layers are then bonded to the monolith structure being formed using a suitable adhesive, or by a co-curing process.

The first, or primary separation channel 32 is formed between two layers 70, 72 of a deposited material having a high dielectric constant. Contour resistors 74,76 and frit material 78 comprise a layer sandwiched between the dielectric layers and define the sides of the first channel. The first channel has a high aspect ratio rectangular cross section (50 $\mu$m×4000 $\mu$m) that forms a continuous 18 cm long enclosed primary channel containing an electrolyte. The shape provides good EOF bulk flow and heat transfer characteristics due to the small size in one dimension, but allows greater fluid volume due to the large size in the other dimension. One end of the channel terminates into a reservoir of buffer solution (not shown) with an upper electrode (+/− high voltage supply), while the other end of the passage terminates into a reservoir of buffer solution that is at ground potential (lower electrode). In the illustrated embodiment, anode 80 is connected to a power source 18 and the cathode is at ground potential. An analyte sample is injected into the primary channel via a small passage (sample port) 82 near the lower electrode (cathode, not shown). The sample will be conveyed by EOF toward the separation portion adjacent the contour resistors 74, 76, where primary separation will occur as discussed above. It is well to note that the contour resistor configuration overcomes an inherent problem of localized variation in electric field intensity as analyte species concentrate at a location, which tends to unfocus the fluid segments or bands forming, by providing a shunting current path around the fluid segment.

In one embodiment additional distributed resistors can be provided in the form of longitudinal strips 81 disposed on the top, bottom, or both top and bottom, of the channel 32. This configuration provides a capability of obtaining both a shunting contour resistance (and hence an electric field intensity gradient continuum) and a zeta potential adjacent the same surface(s) within the channel. If the deposited resistive layer is very thin it is possible to have both a zeta potential and a resistor on the same surface, and hence the longitudinal strips could be replaced by a thin resistive layer over one or both of the upper and lower sides of the channel 32.

A high aspect ratio rectangular channel 32 is used over a round capillary to increase sample volume without adversely affecting the removal of heat. Another reason for using a rectangular capillary is the rectangular shape is compatible with forming planar capacitors for control surfaces. These will be further discussed below. The first channel provides a sample capacity that is approximately 100 times larger than a conventional 50 $\mu$m diameter capillary (for linear separations), and the monolith contemplated offers improved means of dissipating the increased thermal load (from 1 watt for the 50 µm bore capillary to 25 watts for the monolith). Along the 4000 µm upper and lower sides of the channel, the channel is defined by the top and bottom dielectric layer 70, 72. Each is about 125 µm thick and formed of a dielectric material comprising ceramic loaded titanate having a permittivity of about $3.00 \times 10^{-9}$ F/m). Each in turn has a distributed resistor 84, 86 laminated to its surface on a side opposite of the first channel 32. Thus, two plane parallel capacitors are formed on opposite sides of the channel with the buffer acting as the common conductor and the two distributed resistors each acting as the second conductor for each capacitor. These distributed resistors cooperate with the dielectric layers and buffer (electrolyte) solution to form a second electric field generator or electroosmotic flow generator adapted to provide fine control of EOF-induced bulk flow.

Figure 9:
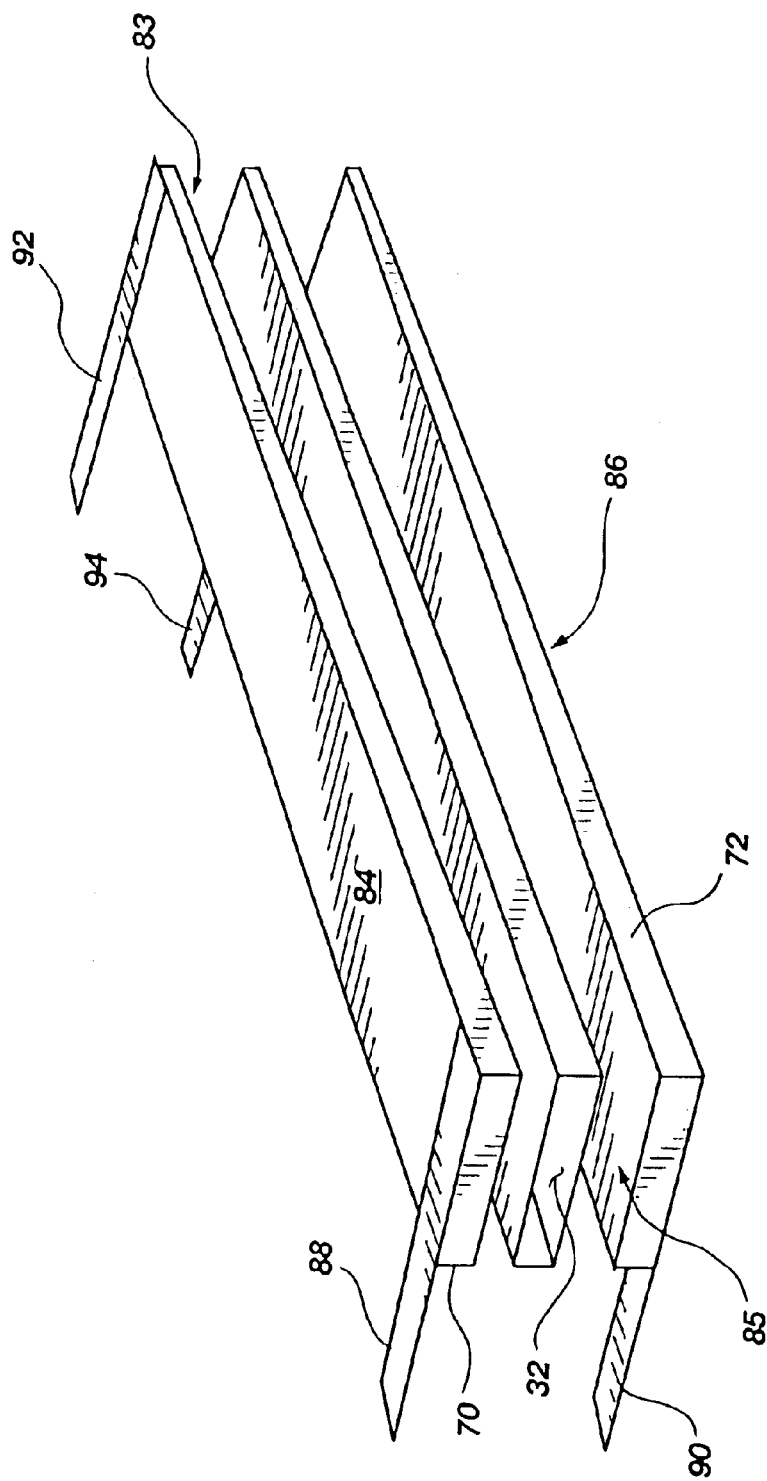
FIG. 9 is a schematic perspective view of a portion of the system shown in FIG. 3.

This can be more readily visualized with reference to FIG. 9, wherein like reference numbers refer to like elements, though not necessarily identical elements (as they do throughout this disclosure). Control surfaces 83, 85 on the dielectric layers 70, 72 have variable zeta potentials due to the distributed resistors 84, 86 deposited on the opposite sides of the respective dielectric layers. The use of an external voltage to control the zeta potential of a capillary was first proposed by Blanchard and Lee as discussed above. Since then, several other researchers have disclosed other variations of this method. However, all of these references disclose conventional capillaries and rely on fused silica as the structural material, resulting in a small bound charge being impressed on the bore. In the Blanchard and Lee patent, an applied voltage of 6,000 V across the wall of a fused silica capillary was barely able to reverse the EOF because the bound charge generated at the inner surface of the bore appears to be only about 0.21 µcoulombs (estimated). Since fused silica has a low dielectric constant (4.2) and has a very active surface, the voltage required to reverse the EOF was very large., However, by reducing the surface activity of the wall, decreasing the wall thickness, and increasing the dielectric constant, a much lower voltage may be used to effect large changes in the EOF, including a polarity reversal.

The thick filth distributed resistors 84,86 and the low surface activity dielectric layers 70,72 each form the equivalent of a planar capacitor with the electrolyte solution in the channel 32 and have a capacitance that is determined by the following equation:

$$C = A\epsilon/L$$

where A is the area (18 cm×4000 µm), $\epsilon$ is the permittivity of ceramic loaded titanate ($\epsilon = 3000 \times 10^{-12}$ F/m), L is the thickness in meters (125 µm), and C is the capacitance in farads (©=17.3 nF). Once the capacitance is known, the bound charge at the interface can be calculated as follows:

$$q = CV$$

where q is in coulombs. For V=100 volts, q=1.73µ coulombs. Early attempts to alter the EOF of a capillary by an external voltage were not practical because the applied voltage varied significantly over the length of the capillary, resulting in an apparent velocity that was not predictable. Since the electrolyte voltage linearly decreases along the length of the channel, the control surfaces must follow the same profile, but be offset by a fixed amount in order to obtain a constant EOF along the channel length. This requires that each control surface 83, 85 have floating voltage sources 88, 90, 92, 94 at both the anode and cathode ends of its distributed resistor. These are digitally controlled by a microprocessor-based controller (not shown) such as a computer interfaced to an isolated D/A converter and high voltage amplifier. This interface, is through an optical isolator of conventional configuration or an optical waveguide connected to a transmitter and receiver.

An inherent advantage of this configuration is that by applying a different potential to the upper control surface 83 than the lower surface 85, a transverse, or "orientation," electric field can be produced which tends to orient polar molecules (such as proteins and DNA fragments) more uniformly. This makes it possible to have a further tool in separation as it makes it so that differences in mobility due to geometry and size are accentuated.

Returning to FIGS. 6, 7 and 8, the shape of the upper and lower distributed resistors 84, 86 can be varied to match that of the contour resistor and channel profile. These distributed resistors are about 15 µm thick, and connection to the floating voltage sources is by conductors formed as unitary extensions of the film or by separate elements as shown. As will be appreciated, the triangular shape shown for the contour resistors is a simplification. In another embodiment the triangular shaped contour resistors 74, 76 are replaced by those having a shape which is defined at least in part by an exponential function of position within the separation portion 36. For example, the width of the contour resistors at the end closest to the anode 38 is zero, and widens toward the cathode 42 according to a function wherein the distance to a position along the longitudinal axis is raised to the fourth power; and that value defines the width at said position. A constant can be used to size the contour resistor at the cathode end to give the desired range of change in resistance over the separation portion.

Both the contour resistors 74, 76 and the distributed resistors 84, 86 can be made of the same material deposited in the same way in the structure.

As currently contemplated, the configuration illustrated is formed by known silk-screen techniques, applying layers in turn on the glass substrates (not shown) which sandwich the configuration within the monolith (not shown). Other masking techniques for forming the configuration are considered possible as well. Depending on scale, other known fabrication methods, such as forming a laminate of pre-formed layers, selective deposition of layers and/or removal of portions of same my masking and photolithography techniques can be employed.

Materials selection criteria include compatibility with the analyte sample(s) contemplated, for example low tendency for adsorption of analyte molecules, minimal interaction with electrolyte solutions, and minimization of other interaction which might affect test results. Suitability and compatibility of materials with the separation method is essential. Fused silica has conventionally been used to form capillary channels used in CE. Acids and bases etch fused silica, resulting in the inner wall of the capillary being eroded. The erosion generates new surfaces with varying concentrations of trace metals and chlorine, which in turn affects the EOF. Inert inorganic materials (silicates, nitrides, carbides, etc.) erode at a tiny fraction of the rate of fused silica, and result in lower EOF over a broad range of pH and have significantly less variation in EOF. Accordingly it is contemplated that these or similar materials are preferable in selecting materials for the dielectric layers 70, 72, the frit, or spacer glaze layer 78, and contour resistors 74, 76. The significance of this conclusion is not to use fused silica but, instead, focus on refractory silicates such as an aluminosilicate frit with more refractory materials such as $Cr_2O_3$, NiO, $TiO_2$, and the like, which are compatible with thick film inks (coefficient of expansion and melting point) and are inert. As will be appreciated, this facilitates screen-print-like fabrication techniques. Materials contemplated for the dielectric layers are currently widely commercially available, for example from Heraeus, Inc. Cermalloy Division of Conshohocken, Pa. It is presently preferred to use lead oxide as the frit material. Other glassy constituents consist of ruthenium oxide, rhodium oxide, cobalt oxide, cadmium oxide, barium titanate, gold and silver. These materials are screened onto glass ceramic substrates. The substrates and inks are identical to thick film hybrids, except in this case the number of screened layers is higher. The thick film inks are classified as glazes, conductors, dielectric materials and resistors. It is contemplated that it may be possible to develop suitable component materials based on alumina silicate frits, which are more chemically inert.

A detector 96 comprising electrodes 98, 100 is positioned adjacent the separation portion 36 of the channel 32. The detector is based on the analytes having a higher resistivity (>120 $\Omega$-cm) than the electrolyte, which is believed to be the case for all of the proteins in blood or spinal fluid. The two electrodes (50 $\mu$m×15 $\mu$m cross section) extend laterally into the channel immediately above the electric field intensity gradient. The space between the electrodes (4000 $\mu$m) forms the feedback resistor of an electrically isolated operational amplifier. The operational amplifier is fed by an adjustable DC source. For a 200 $\Omega$-cm electrolyte, the resistance between the two electrodes is 6.4 megohms. With a feed forward resistance of 64 megohms and an input voltage of −100 mV, the operational amplifier output would be approximately at +10 mV. Therefore, the dynamic range of the detector is approximately three decades (10 mV to 10V). The channel volume enclosed by the electrodes is $3\times10^{-12}$ $m^3$ or 3 nL and when combined with the dynamic range results in a minimum detection volume of 3 pL, which may be further lowered by reducing the DC input reference. This assumes that the concentrated protein band has a much higher resistivity than the electrolyte. Above 10 volts, the amplifier circuit of the detector is designed to limit the output voltage to avoid amplifier saturation. The analog output is fed into a 5,000 V isolation amplifier and then fed to an A/D converter for digital storage. The present objective of the detector is to only detect the separated proteins. A contemplated alternative embodiment is to quantitate the separated analytes using a much more sophisticated detection system.

The detector 96 can provide quantitative information. If the separated analyte species band passes the detector with a constant velocity the measured impedance between the two electrodes 98, 100 will change in such a way that the output of an amplifier (not shown) connected to the electrodes will change with time to reflect passage of the analyte species band. The analyte band will have a Gaussian distribution, and the output function with time will be a Gaussian curve if the baseline is subtracted assuming the detector is not saturated (a rectangular, or clipped, curve yielding no quantitative information). The area under the output curve and the net velocity of the analyte band can be used to quantify it. This can be done by a piecemeal integration, again subtracting the baseline output.

A more sophisticated detector 96 can be used, which incorporates an amplifier circuit that changes its gain depending on the size of the change in input signal. Such an amplifier might have a variable gain enabling a detection range of 6 or 7 decades, rather than 3 decades. An analog gain changer (widely commercially available, for example from Burr-Brown, Inc.) cooperating with the A/D converter of a detector circuit, as well as a programable gain changer at the input of the detector amplifier, for example, controlled by a microprocessor, would keep the A/D converter at mid-range by changes made by the gain changers. Knowing the settings of the gain changers and the output of the A/D converter, the amplitude of the signal is known though it otherwise would be beyond the range of detection. AC noise sources (in electrolyte, power supplies, etc.) limit the dynamic range.

Additional qualitative information may be obtained from the simple two electrode 98, 100 detector 96 by adding a sweep frequency source that sweeps over a range of about one or several hundred hertz to about one or several megahertz. By monitoring the decrease in amplitude and phase shift of the signal as an analyte band passes by the electrodes a characteristic reactive impedance with respect to frequency, which is individual to different analyte species (such as different proteins or classes of proteins) can be detected. By investigation of the relationship of this reactive impedance with frequency by a processor having programing comprising a statistical method such as partial least squares with latent variable (PLS), at least partial information concerning composition of the protein or other analyte can be obtained. This technique is probably not going to yield information as specific as that obtainable from more sophisticated, and costly, instruments such Asia time-of-flight mass spectrometer, but it will be appreciated that a stand-alone instrument with such a detector can be made which is suitable for confirming the presence or absence of a specific known analyte such as a protein. As an example, a low cost instrument, even a disposable, comprising a primary separation channel 36 and such a detector 96 could be used to test for the presence or absence of a specific class of proteins in a blood sample.

Another consideration should be recognized with respect to DC impedance measurement across the electrodes 98, 100 of the detector 96. Polarization, comprising residual charge, in the materials around each electrode, can affect the accuracy of the detector. To mitigate this, additional reference electrodes (not shown) can be provided. Also, periodically switching the direction of current across the;detector electrodes can mitigate the problem.

It will be understood that other factors, such as placement to minimize electric field intensity gradient between the electrodes, chemical interactions, and the like, which can affect accuracy of detections, will be minimized.

With reference again to FIG. 8, two lateral field electrodes 102, 104 can be placed outboard of the channel 32 and electrodes 74, 76. These lateral field electrodes enable further fine control of separation of analytes. For example, they can be used to separate like molecules of differing length. As will be appreciated the longer a molecule is, the greater the difference in mobility in a longitudinal direction as compared with mobility in a transverse direction. Also, the longer it is, the more "stiffened" it is generally in the presence of the longitudinal electrical field compared to a normal state. Applying a lateral AC electric field will tend to rotate, or at least "wiggle" polar molecules, and the longer the molecule the more this effect will tend to influence its mobility in a direction parallel with the longitudinal axis of the channel 32 and the EOF induced flow of the electrolyte solution as the frontal area exposed to the flow will be greater.

The wide channel (4000 ($\mu$m) also generates a small lateral field gradient (bow), which affects the quality of the separation. This effect may be corrected by using spatially shaped electrodes bowed opposite to the bow in the field lines (not shown) adjacent and downstream of the separation portion 36 and/or adjacent the analyte concentrator 52, which would remove most of the distortions.

While the difference in potential described above facilitates an orienting electric field to align polar analyte molecules in a first direction, a second transverse orientation field can be applied to further aid in distinguishing analyte species. With reference to FIG. 8 particularly, lateral field electrodes 102, 104 can be laid down adjacent the channel, but outboard of the contour resistors 74, 76. These further electrodes can be brought to different potentials to further alter molecular orientation. Broadly speaking, they provide one more control parameter that can be adjusted to enhance system performance.

Figure 10:
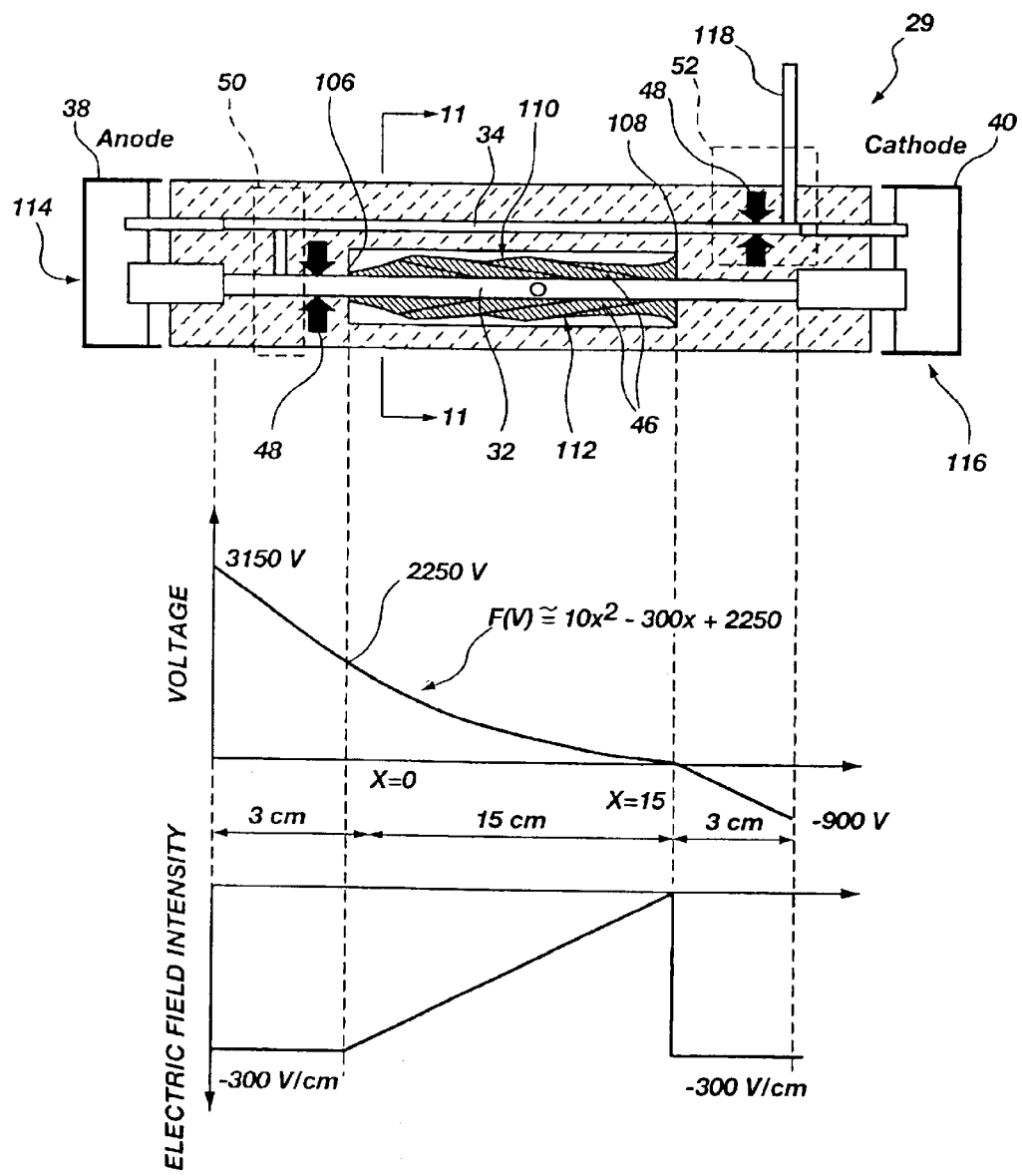
FIG. 10 is a diagram illustrating a system in accordance with principles of the invention.
Figure 11:
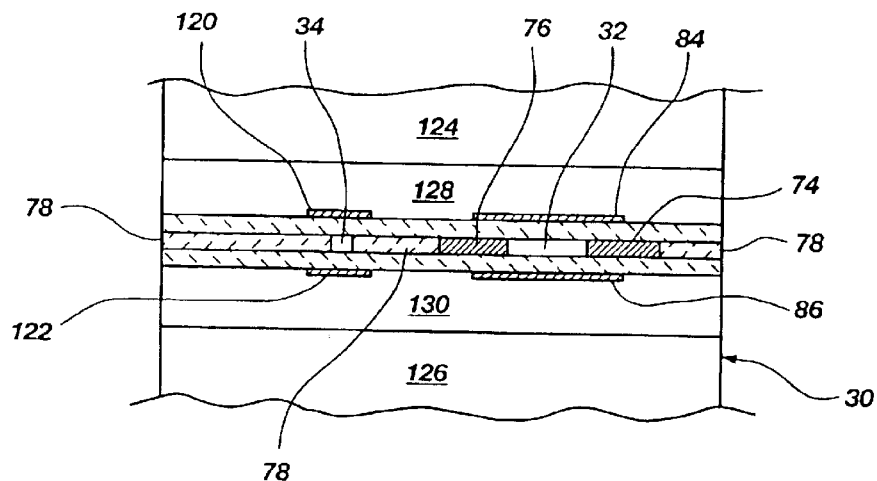
FIG. 11 is a crossectional view, taken along line 11—11 in FIG. 10, illustrating the configuration of the system shown in FIG. 10 in one embodiment.

With reference now to FIGS. 10 and 11, further details and variations of the design of the system 29 will be discussed. To design the first separation channel 32 for a specific task, for example to separate most of the proteins in a sample comprising blood, we initially need to know what the distribution of protein mobilities are in blood and their concentration. Unfortunately, the state of the art apparently does not provide practitioners the "tools" to answer this question. Therefore, we need to make some rough assumptions. The first assumption is that proteins have mobilities between $10 \times 10^{-4}$ cm$^2$/V-sec to $10 \times 10^{-6}$ cm$^2$/V-sec and a differential mobility between proteins of $2 \times 10^{-8}$ cm$^2$/V-sec, or approximately 50,000 cations and 50,000 anions and these 100,000 proteins have concentrations greater than 10 pL in a blood sample of 1 $\mu$L.

Based on these assumptions, we start with a channel 32 that is about 4000 $\mu$m wide, has a 50 $\mu$m height approximately, and is about 21 cm long. A set of distributed contour resistors 46, each 15 cm in length and about 12 $\mu$m thick, are placed centrally in the channel. The resistors are in the plane of the channel and contact the channel in the 50 $\mu$m height dimension forming a portion of the wall (12 $\mu$m out of 50 $\mu$m), and cause a resistive shunt to be formed with the electrolyte in the main channel as set forth above. Each resistor is geometrically shaped or has varying resistivity with longitudinal length to cause a nonlinear voltage gradient within the channel. If the resistors are shaped, then at the anode side, the distributed resistors are thin, (a high resistance), while at the cathode side the resistors are wide, (a much lower resistance). The shape of the contour resistors causes the channel voltage gradient to vary in a predictable manner. A constant width resistor has a linear voltage drop per increment of channel distance, while contoured resistors cause the voltage drop per increment of channel to vary. The voltage gradient of the electrolyte in the channel can thus be contoured for any monotonic function. For our example, we will shape the electric field intensity to be linear over the length of the gradient starting with $-300$ V/cm at the anode side and decreasing to zero at the cathode side. We can then mathematically define this electric field intensity with the longitudinal dimension (x) as $E(x) = -300 - 20x$ Where $E(x)$ is the electric field intensity at x in V/cm By integrating $E(x)$, we can determine what voltage profile is required to generate the electric field intensity, which results in $V(x) = 10x^2 - 300x + 2250$ Where $V(x)$ is the voltage at point X (Note: the constant was determined by forcing the voltage to zero at x=15 cm)
$V(x)$ generates an electric field intensity $E(x)$ that has a high of $-300$ V/cm to 0 V/cm over the, distance of x=0 to x=15 cm.

R is resistance in ohms
X is channel length in cm
W is channel width in cm
H is channel height in cm Working backwards, we can now determine what EOF is required to equilibrate the slowest protein, since the electrophoretic velocity and the EOF will be equal. This is calculated by selecting an electric field intensity slightly below our 300 V/cm maximum, say 290 V/cm, and then calculating the electrophoretic velocity as follows:

$V_{EOF} = V_{EP} = v_{EP}E = 0.0029$ cm/sec
Where $V_{EOF}$ is the electroosmolic velocity in cm/sec
$V_{EP}$ is the electrophoretic velocity in cm/sec
($v_{EP}$ is the mobility of the slowest protein ($10 \times 10^{-6}$ cm$^2$/V-sec)

The fastest protein ($10 \times 10^{-4}$ cm$^2$/V-sec) at an $V_{EOF}$ of 0.0029 cm/sec requires an electric field intensity of $-2.9$ V/cm. Solving for x in $E(x)$ yields the location of the fastest protein at x=14.855 cm.

Increasing the EOF forces the slowest cationic proteins to migrate to the anode 38. For example, if we look at these two protein extremes, we see that if the EOF is increased to 0.004 cm/sec the force on the slowest protein results in a net velocity of 0.004 cm/sec$-0.003$ cm/sec=0.001 cm/sec toward the anode, while the fastest protein has now been repositioned to x=14.800 cm. Increasing the EOF continues to force more cationic proteins to migrate to the anode until the fastest protein is released at an EOF of 0.3 cm/sec.

To calculate the incremental shunt resistance in parallel with the channel 32 to generate the voltage gradient $V(x) = 10x^2 - 300x + 2250$ requires that $V(x_1 - x_2) = $(current) (equivalent resistance) for each interval $x_1 - x_2$ $R_{eq} = (R_C)(R_R)/(R_R + 2R_C)$
Where $R_{eq}$ is the equivalent incremental resistance
$R_C$ is the incremental channel resistance
$R_R$ is the incremental contour resistance Solving for $R_R$ yields $R_R = (2)(\Delta V)(R_C)/[(I)(R_C) - (\Delta V)]$ Where ($\Delta V$ is the incremental voltage drop (0.2 cm)
If the interval is 0.2 cm then the incremental resistance for the channel becomes 12 k ohms per 0.2 cm increment.

Figure 12:
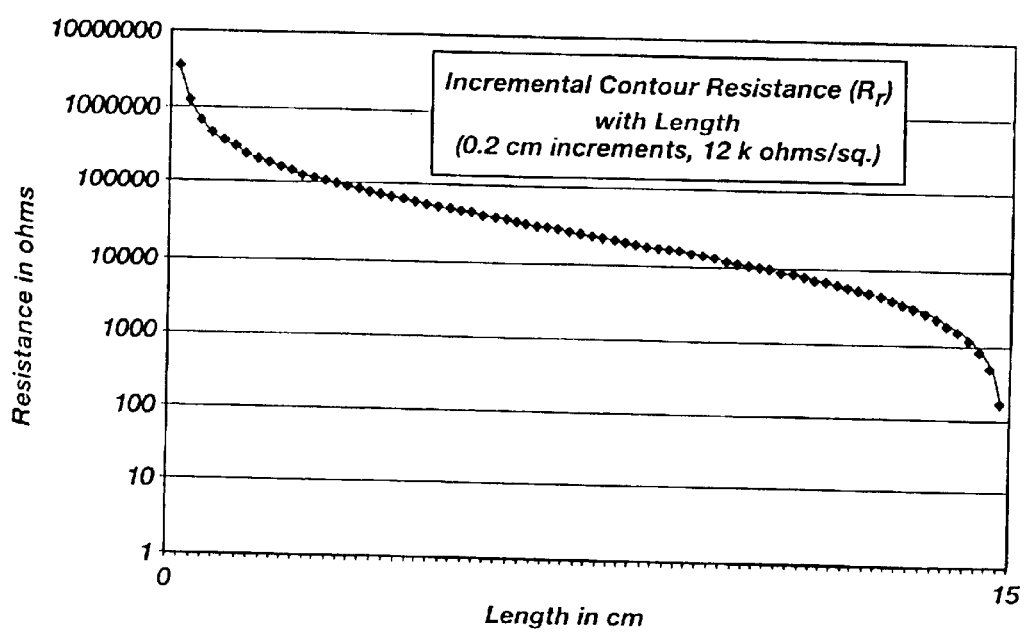
FIG. 12 is a plotting of resistance vs. position along a channel of a contour resistor in accordance with principles of the present invention.

The resulting shunt resistance profile is shown in FIG. 12. Each contour resistor ranges in value from 3.6 megohms at the anode side of the voltage gradient to 161 ohms at the cathode side of the gradient. Therefore, to generate the voltage gradient $V(x)$, each contour resistor must vary in incremental resistance by over 22,000 to 1. This poses a problem because the classical thick film hybrid method of generating a resistance is by forming a two-terminal network where a high value resistor is long and thin, while a small value resistor is very wide and narrow between the terminals (using the same resistivity ink), however, in this example we are concerned with a distributed resistor, not a two terminal device. This means that at the high resistance end of the channel, we would use a very thin geometry (lateral to the channel) in parallel with the channel and at the low voltage end of the channel; we would use a very wide geometry. A wide resistor is self-defeating, since the wider the resistor, the greater the voltage drop laterally within the resistor, which results in the contour resistance seen by the channel reach a minimum value, which then limits the dynamic range of the resistance that may be achieved by a single resistivity thick film ink.

There are several ways of overcoming this limitation. The easiest is to make the contour resistor a two-terminal device by adding a conductor, which is terminated to ground, at its outbound edge (opposite the channel). This would allow a very wide lateral width at the anode and a very narrow lateral width at the cathode. The disadvantage of this method is the increase in power dissipation and voltage break down at the anode end. A second method is to decrease the incremental resistance of the contour resistor by increasing the thickness of the thick film resistor as it approaches the cathode, but this would require very unusual screening techniques to lay down such a structure. A third method, illustrated in FIG. 10, is to apply overlapping geometries of decreasing resistivity inks such that at the cathode end 108 of the contour resistor 46 has a low resistivity and the anode end 106 has a high resistivity with a resistivity gradient between the two ends. The precise voltage profile is then achieved by laser trimming the outboard sides 110, 112 of the geometries. A fourth method is to use ink jet technology to deposit the varying resistivity ink directly from three or four ink resistivities, which are applied using a computer controller to produce the desired resistance gradient. This can be followed by laser trimming. This last approach can also limit the width of the contour resistor to less than half a channel width. For limited resistor excursions of less than an octave, single resistivity ink is adequate but would still require laser trimming. All four of the forgoing exemplary embodiments contemplate fabrication by screen printing, but the concepts can be implemented using other known fabrication techniques.

In the embodiment illustrated in FIGS. 10 and 11, the first and second channels share common fluid wells 114, 116 at their ends. The system further comprises a first analyte detector 48, which detects analytes based on change in conductivity and conductivity differences. A steering valve 50 is provided to steer analytes between channels. An analyte concentrator 52 is included, as is an interface port 118 for connection to a fraction collector and/or mass spectrometry apparatus. The first, or primary, separation channel and the secondary channel each have associated control surfaces and therefore "plates" comprising distributed resistors 84,86 and 120, 122, for controlling the EOF bulk flow in the channels 32. Furthermore, spaces comprising coolant flow paths 124, 126 overlay and undergird the substrates 128, 130 of the monolith 30.

Before turning to other features of the illustrated system 29, it is reiterated that a basic system for separations can comprise only the primary channel 32. A detector 48 can be provided, and/or a port for connection to quantitation and/or qualitation devices (not shown) such as a fraction collector or mass spectrometry instrument. In such an embodiment the analyte species are separated by focusing in the CEFIG of the separation portion 36, then the EOF is increased to drive off the separated analyte bands one by one into the detector and/or a collection port.

Returning to the illustrated embodiment, the steering valve 50 of the system will now be discussed in more detail. The steering valve employs isolated sources to generate electric field intensity barriers at channel interfaces to redirect EOF. The insertion of an opposite polarity electric field intensity relative to the channel electric field intensity over a short channel segment will prevent ions from migrating past the barrier created in that segment, and/or redirect EOF bulk flow into another branch.

Figure 13:
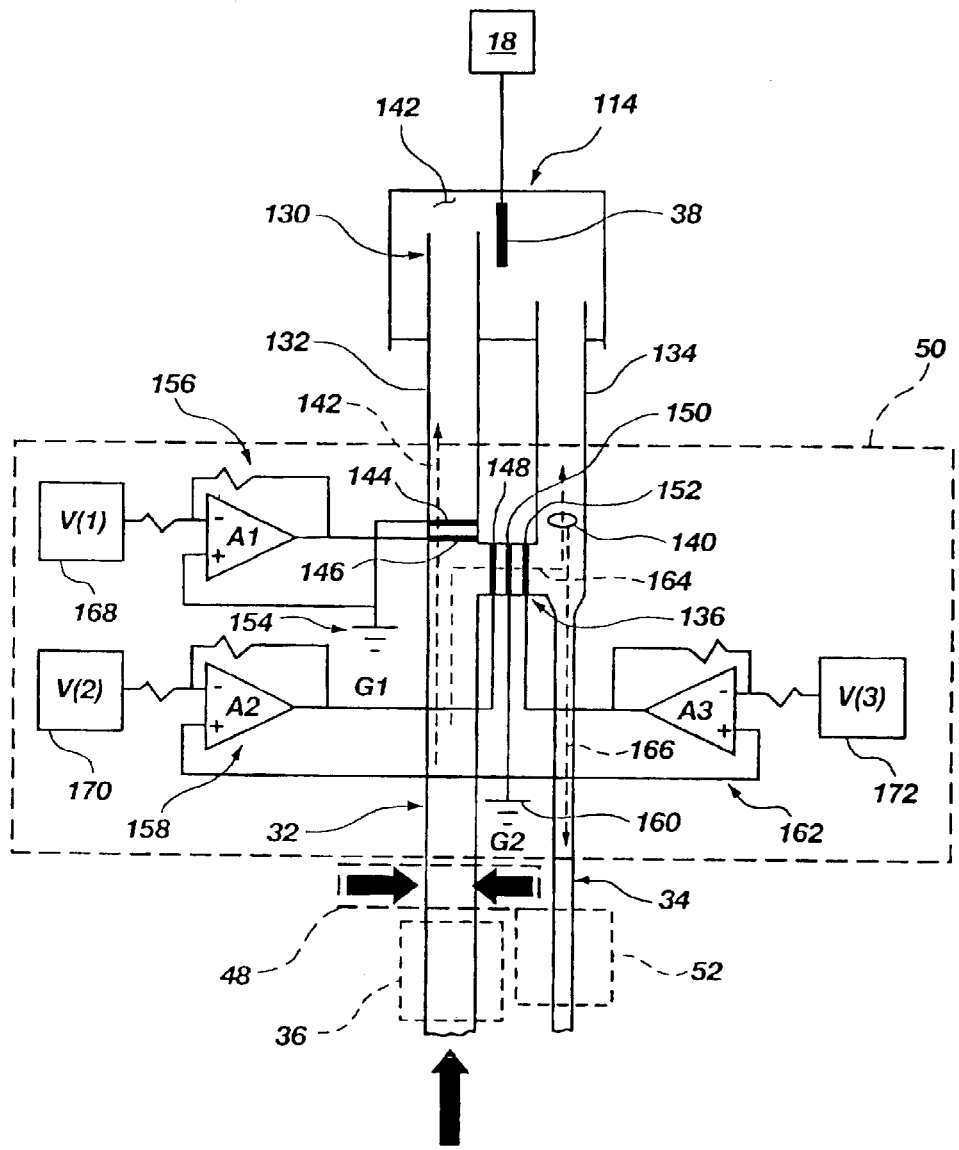
FIG. 13 is a schematic diagram of a steering valve portion of the system shown in FIG. 10; and, FIG. 14 is a diagram illustrating an analyte concentrator in an embodiment in accordance with principles of the invention.

Referring to FIG. 13, a steering valve 50 of the electromobility focusing controlled channel electrophoresis separation system 29 is shown schematically. In the illustrated embodiment, the anode 38 connected to a power source 18 is electrically coupled to an electrolyte solution fluid 138 contained in the first separation channel 32 of the system, and is physically positioned at a fluid well 114 in fluid communication with a first end 130 of a terminating arm 132 of the primary channel 32 and a terminating arm 134 of the secondary channel 34. As will be appreciated, a cathode (not shown) is also electrically coupled to the electrolyte fluid and is positioned similarly at the opposing end (not shown) of the first and second channels. Separate sets of cathodes and anodes (not shown) can alternatively be provided for the primary and secondary channels (e.g., as shown in FIG. 3). As mentioned above, the steering valve 50 is used to direct selected analytes, or, more particularly, analyte species separated and focused into one or more bands, from the primary channel into the secondary channel through a connecting channel 136. An analyte band 140 is shown schematically.

Electrodes 144, 146, 148, 150 and 152 are provided to control flow in the area adjacent an intersection of the primary channel 32 and the connecting channel 136. Preferably when diverting analytes 140 from the primary channel 32 into the secondary channel 34, the steering valve 50 should not interrupt the electroosmotic bulk flow 142 of the primary channel 32. This diversion of analytes from the primary channel to the secondary channel via the steering valve is herein defined as the steering function. An important aspect of the steering function is that it is an isolated function. In other words, the electrodes of the steering valve are electrically isolated from the general function of the system including any functions that also require isolated electrical power or grounding.

Additionally, the electrodes 144, 146 disposed in the terminal arm 132 of the primary channel 32, and the electrodes 148, 150 and 152 disposed in the connecting channel 136 are also electrically isolated from one another as much as possible. This isolation is achieved by using an lip, isolation transformer (not shown) for steering valve power requirements. As is known in the art, an isolation transformer generally incorporates high insulation resistance and high voltage break down between its primary and secondary. Further, all digital/analog input and output signals from the steering valve are electrically isolated except the output drive voltage to, the electrodes in the respective channels.

A brief explanation of the provisions, for isolation of the inputs and outputs to the steering valve 50, which discussion can have application in control inputs and outputs to and from other system elements is deemed warranted. If the signal is analog, then a Burr Brown analog isolator can be used in either direction. If the signal is digital, then an optical isolator is used. Generally this comprises a light emitting diode illuminating a phototransistor; or, an optical waveguide is used. In the later case, a transmitter converting a digital electrical signal to an optical signal is located at one end. A photo diode is located at the other end, and cooperating with a transresistance amplifier, functions to convert the optical signal to digital electrical signal. Additional electronics, comprising a microprocessor can be provided at the transmitter and receiver to encode and decode the optical signal. A bi-phase encoding technique (Manchester code) can be used. All power supplies to the isolated functions of the system 29 use high insulation resistance between the primary and secondary.

In the case of the steering valve 50, generally there are several supply voltages required to operate the isolated function, for example +/−5V, +/−15V, and +/−150V. High voltage amplifiers (+/−100V swings) are used. The isolated electronics of the steering valve can also include analog functions, and a microprocessor programed to encode/decode bi-phase optical signals mentioned above, and perform local operations such as forming ramp voltages within the channels and/or turning on or off electric fields within the channels with proper rise times and fall times. The microprocessor can also include local internal auditing of local functions.

Controlling the isolated steering function may be accomplished by applying a drive voltage between two closely spaced primary electrodes 144, 146. A first ground electrode 144 is connected to an isolated ground (G1) 154 and the other 146 is connected to an output of a first amplifier (A1) 156. These electrodes provide line sources of potential and the voltage is dropped between these primary electrodes 146, 144 across the volume of electrolyte fluid 138 disposed therebetween. These primary electrodes 144, 146 are preferably placed within the primary channel 32 at a distance of about 1–5 mm apart. This configuration facilitates an ability of the primary electrodes 144, 146 to generate localized electric field intensities that are of positive or negative polarity having varying amplitudes of up to several times the electric field intensity of the primary channel 32, as the primary electrode spacing and amplifier output determines the electric field intensity locally. The same is true of branching electrodes 148, 150 and 152 Within the connecting channel 136. The electric fields discussed herein with respect to the steering valve 50 are not to be confused with existing electric fields present in the primary channel 32 and the secondary channel 34. The electric fields associated with the steering valve 50 are superimposed on top of the electric fields generally present in the primary channel 32 and secondary channel 34 and are essentially independent of those electric fields within practical, limitations.

The primary channel 32 and the secondary channel 34 are intended to operate independently of each other except when an analyte band 140 is to be transferred from the primary channel 32 through the connecting channel 136 and into the secondary channel 34. As alluded to above, the steering valve 50 preferably is comprised of two groups of electrodes, the primary electrodes 144, 146 are found within the primary channel 32. Branch electrodes 148, 150, 152 are found within the connecting channel 136. The primary and branch electrodes are each powered from separate isolated power supplies. The primary electrodes 144 and 146 are connected to an isolated ground (G1) 154 and a first operational amplifier (A1) 156, respectively. The branch electrodes 148, 150, and 152 are connected to a second operational amplifier (A2) 158, a common second isolated ground (G2) 160 and a third operational amplifier (A3) 162, respectively.

The primary electrodes 144, 146 function as a gate in the primary channel 32 and the branch electrodes 148, 150 and 152 act as an isolation barrier to separate the primary channel 32 and the secondary channel 34 from each other when no analytes 140 are being transferred through the connecting channel 136. During an operational state where no analyte transfer though the connecting channel occurs, output of amplifier A1 is biased slightly negative with respect to ground G1 such that the primary electrodes in the primary channel 32 create no local discontinuity in the electric field intensity in their location(s) in this sector of the primary channel 32. Also during this mode of operation, the outputs of both amplifiers A2 and A3 are biased such that the branch electrodes 148, 150, 152 generate a local discontinuity in electric field intensity. This electric field intensity discontinuity is opposite in polarity to that found in the primary channel 32 and the secondary channel 34. This effectively isolates the primary channel 32 from the secondary channel 34, and thus, the EOF driven bulk flow 142 in the primary channel is not disrupted. Electrolyte fluid flows past the primary electrodes into the terminal arm 132 of the primary channel.

The primary detector 48 detects analyte bands 140 moving towards the steering valve 50. The detector can also determine the concentration of the analyte species comprising the band using methods discussed above giving an output signal curve showing the Gaussian distribution of the analyte in the electrolyte solution flowing past the detector electrodes (98, 100 in FIG. 8). This information is used by the controlling computer (not shown) to divert the analyte band 140 in the EOF driven flow 142 from the primary channel 32 and transfer it to the secondary channel 34 via an alternative EOF driven flow. In the illustrated embodiment, the primary detector is placed adjacent and downstream from the separation portion of the primary channel 36 having a continuous electric field intensity gradient, such that the detector detects analyte 140 concentration as it passes out through a downstream end of the electric field intensity gradient. The controlling computer (not shown) operating the steering valve 50 will transfer the analyte 140 from the primary channel 32 to the secondary channel 34 by first timing the arrival of the analyte band 140 at the location where the connecting channel 136 joins the primary channel 32 and then changing the operational state of the system by switching the voltages applied to the primary electrodes 144, 146 and branch electrodes 148, 150 and 152 to force the analyte band 140 to flow through the connecting channel and into the secondary channel 34 as discussed below. Once the analyte band 140 has entered the secondary channel 34, the primary and branch electrodes are switched back to return the system to the first operating state condition as defined previously.

Once the analyte band 140 has been transferred to the secondary channel 34 via the alternative EOF driven flow 164, if it is desired to concentrate the analyte band 140 further, the analyte band 140 having a low concentration may be moved into the analyte concentrator 52. This is accomplished by a polarity reversal of the control surfaces (not shown) of the secondary channel 34 resulting in an EOF reverse driven flow 166 in the secondary channel. Thus, the analyte band 140 is moved to the analyte concentrator. Once the analyte band 140 is at the analyte concentrator, the EOF reverse driven flow is reduced to affect a desired analyte concentration as will be discussed below. Once concentrated, the EOF reverse driven flow 34 is again increased to drive the focused analyte band 140 out of the analyte concentrator to a desired location within the monolith, e.g., a port to a fraction collector or a mass spectrometry device (not shown).

A major consideration in the design of the steering valve 50 is to not interfere, or at least minimize interference with, the electroosmotic force acting in the primary channel 32 when transferring analytes from the primary channel to the secondary channel 34. This is accomplished in the illustrated embodiment in part because the terminal arm 134 of the secondary channel 34 is configured so that it cooperates with the connecting channel 136 to provide an identical EOF regime as the terminal arm of the primary channel. The connecting channel and the terminal arm of the secondary channel each has the same cross section as the primary channel. The combined length of the connecting channel and terminal arm of the secondary channel is made equal to that of the terminal arm of the primary channel. Therefore, this latter combination of channels has as near as possible the same EOF regime as the terminal arm 132 of the primary channel 32. Since EOF is a bulk property of the entire channel of flow, any change in cross section or change in electric field intensity along the channel of flow would alter the EOF. Therefore, when transferring analytes 140 from the primary channel 32 to the secondary channel 34, the cross section and the channel length is kept constant due to geometry of the system. As will be appreciated, in another embodiment separate wells 114 and anodes 38 can be provided for each of the terminal arms, and the potential at each anode be made the same to achieve the same result.

To illustrate the effect of applying various electrical potentials to the primary electrodes 144, 146 and the branch electrodes 148, 150 and 152, the following examples are given. First, when the primary electrodes are biased with a large positive voltage relative to the first isolated ground (G1) 154, a positive electric field intensity is generated in the segment between the primary electrodes which prevents EOF bulk flow 142 from occurring in the terminal arm 132 of the primary channel 32. At the same time, if the branch electrodes within the connecting channel 136 are switched to potentials as needed to form an electric field intensity through the connecting channel that is identical to that formerly extant in the terminal portion of the primary channel, the alternative EOF driven flow 164 is formed through the connecting channel to the terminal arm 134 of the secondary channel 34. In order to optimally form the desired electric field intensity using the branching electrodes 148, 150 and 152, the branched electrode 148 nearest the primary channel 32 is biased slightly negative with respect to the second isolated ground (G2) 160, and the branching electrode 152 nearest the secondary channel 34 is biased slightly positive with respect to G2.

When the primary electrodes 144, 146 are biased with a slightly negative voltage relative to the first isolated ground (G1) 154, and the branch electrodes 148, 150, 152 are brought to potentials preventing EOF bulk flow through the connecting channel 136, the EOF flow in the primary channel 32 flows into the terminal arm 132. The branch electrodes act to prevent flow through the connecting channel by biasing the branched electrode 148 nearest the primary channel 32 with a positive charge with respect to the second isolated ground G2 160, and biasing the branched electrode 152 nearest the secondary channel 34 negatively with respect to G2. This creates a positive electric field intensity locally, which prevents EOF bulk flow between the primary and secondary channels through the connecting channel. The forgoing is true when the primary channel 32 and the secondary channel 34 have a negative electric field intensity such as when separating cations. As will be apparent if the polarity in the primary and secondary channels is reversed, the polarities described above with respect to the steering valve will also need to be reversed.

The forgoing discussion of the steering function assumes computer control as mentioned. Control voltages V1, V2, V3 applied from electrically isolated sources (168, 170, 172, respectively) controlled by the computer controller (not shown) result in the applied potentials at the primary and branching electrodes 144, 146, 148, 150 and 152.

Figure 14:
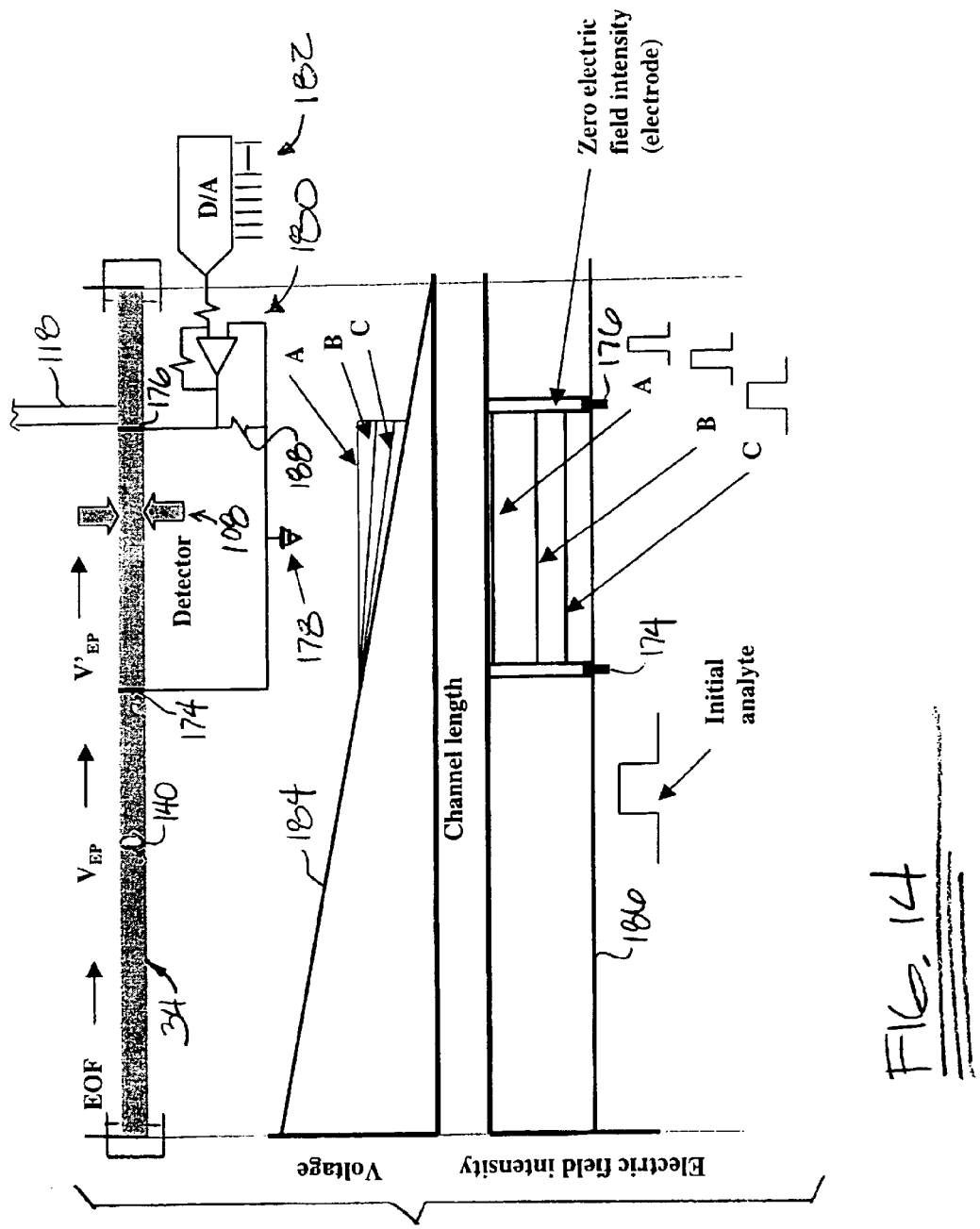

Turning now to FIG. 14 and discussion of the analyte concentrator 52 there schematically illustrated, it will be appreciated that the analyte concentrator comprises first 174 and second 176 electrodes connected to an isolated ground 178 and the output of an operational amplifier 180 connected to an interface with the computer comprising a controller (not shown), for example by means of a digital/analog converter 82. A secondary analyte detector 108 is also included. An interface 118 with a fraction collector or mass spectrometry device is positioned so as to receive concentrated analyte bands 140 from the analyte concentrator.

In explanation of the operation of the analyte concentrator, it will be recalled that when an analyte molecule moves through a channel, such as the secondary channel 34, its velocity is determined by its charge, shape, and the magnitude of the electric field intensity of the field propagated in the electrolyte solution, as well as the EOF bulk flow. If the electric field intensity is intentionally changed to a lower value in front of an analyte band 140, then when the analyte band leading edge begins to pass into this lower field, the longitudinal dimension of the analyte band will begin to compress, since the trailing edge of the analyte is still moving at a higher velocity. The degree of compression is defined by the following equation:

$$\underline{W'} = \underline{V_{EOF} \pm V'_{EP}}$$
$$W V_{EOF} + V_{EP}$$

Where W' is the compressed analyte width (cm)
W is the initial analyte width (cm)
$V_{EOF}$ is the electroosmotic flow velocity (cm/sec)
$V'_{EP}$ is the electrophoretic velocity in the lower electric field (cm/sec)
$V_{EP}$ is the electrophoretic velocity in the higher electric field (cm/sec)

If control surfaces (not shown) provided above and below the channel 34 are set to zero value applied potential, and the electric field intensity in the analyte concentrator is set to a low value, then there is no $V_{EOF}$ and $V'_{EP}$ approaches zero, thus, creating a very narrow analyte peak. The voltage gradient profile 184 on the voltage versus channel position plot illustrated shows a change in the voltage profile, including several exemplary profiles A, B and C created by the isolated amplifier 180 driving the first 174 and second 176 analyte concentrator channel electrodes. The bottom diagram plot portion shows the profile 186 of electric field intensity versus channel position plot. Varying the voltage on the electrodes results in varying electric field intensity between the two electrodes, including exemplary profiles A, B and C corresponding to those of the voltage profile 184. If the voltage applied to the electrodes were adjusted to bring the electric field intensity to a zero value between the electrodes, this would create a near infinite "peak" or thin analyte band; however, the peak would be stationary. To keep the analyte band 140 moving, the voltage gradient is set to a greater value than zero, or the voltages on the control surfaces are set at some minimal value. For example, for a cation with a moderate mobility, no EOF in the channel, and the electric field intensity of the analyte concentrator set at ¹⁄₁₀₀ of the channel field, the analyte peak will: theoretically be compressed by a factor of 100.

Others working in the separation arts have described analyte concentration using a pH gradient, a small pore gel, displacement electrophoresis with a hydrodynamic counter flow and using dialysis tubing, but not using isolated voltage sources. However, their basic approach was to alter the electric field intensity in one segment of the capillary or channel used. The approach disclosed herein offers greater flexibility in optimizing the degree of compression of the analyte band 140, or in other words, better focusing of a separated analyte species.

It will be noted with interest that a byproduct of the concentration is a highly concentrated analyte resulting in a dramatic increase in the resistance of the analyte, which would result in al large voltage drop across the analyte band 140 and accordingly reduce the electric field intensity forward of the analyte. To keep the electric field intensities at a reasonable level, a shunt resistor 188 can be placed in parallel with the analyte concentrator. The shunt resistor does not limit the degree of concentration of a trace analyte.

For a very small sample volume, concentrating the one or more analyte species does not result in a increase in channel resistances so significant as to seriously degrade performance when the shunt resistor is provided. However, if the sample volume is comparatively large, after concentration each band of concentrated analyte species has a significant longitudinal extent, and a longer current path through the shunt resistor results. This does effect the channel current and limits performance. Therefore small sample volumes are preferred.

Throughout the system 29, when electrodes are present in the channel there is a possibility that a discontinuity in the electric field intensity will result. One way this can be mitigated is to form the electrodes from a resistive material so that the resistance of the electrode material matches that of the electrolyte solution. The electrode in each case is connected so that voltage drop across it is minimized. For example a line source electrode extending across the channel 32 such as electrodes 174, 176 of the analyte concentrator or the steering valve (144, 146, 148, 150 or 152 in FIG. 13) is connected at each end on opposite sides of the channel in one embodiment. In another embodiment an electrode can comprise two layers, one layer in contact with the channel being formed of a resistive material matching the resistance of the electrolyte, the other layer (being shielded from the electrolyte) can be conductive. In the later embodiment the electrode is brought to the same potential along its entire length.

Another comment pertaining to the system 29 as a whole is that it enables movement of analyte species around the system, through channel intersections, etc. by precise manipulation of EOF-induced bulk flow in channels. This has implications beyond the system disclosed. Miniaturization of the elements discussed can enable such manipulations in "lab-on-a-chip" applications for example to move substances from one point to another, mix them at a desired point, etc.

With reference again to FIGS. 3, 7 and 11, it will be appreciated that the forgoing discussion sets forth an integrated system for separations which can all be incorporated in the monolith 30 construction given as an example. Implications for improved separations and enablement of heretofore untried diagnostic procedures will be apparent to those skilled in the art. While particular forms of the invention have been illustrated and described, it will also be apparent that various modifications can be made without departing from the spirit and scope of the invention.

What is claimed is:

1. A liquid-phase electromobility focusing separation system configured to separate at least one discrete analyte species from an analyte sample, comprising:
    a first separation channel defined by a confinement enclosing an interior channel volume, said first separation channel having first and second ends and a longitudinal axis, and said first separation channel being configured to contain an electrolyte solution within the interior channel volume, said separation channel providing the only flowpath for both the analyte sample and the electrolyte solution;
    a continuous electric field intensity gradient generator configured to apply a electric field intensity gradient within the first separation channel along the longitudinal axis over at least a portion of the first separation channel intermediate the first and second ends, the intensity of electric field generated varying as a continuous function of location along the longitudinal axis, whereby electrophoretic migration of an analyte species within the first separation channel is actuated by a force that varies with position along the longitudinal axis as a continuous function of position along the longitudinal axis within said portion of the first separation channel;
    an electroosmotic flow generator configured to generate an electroosmotic flow along the longitudinal axis of the first separation channel, which electroosmotic flow is variable as to at least one of: (i) the magnitude of the flow, and (ii) the direction of the flow, to enhance separation of said at least one analyte species by enabling separation control of an interaction of forces it created by the continuous electric field intensity gradient generator and the electroosmotic flow generator.

2. A system as in claim 1, wherein the electroosmotic flow generator comprises a power supply and a distributed source of potential positioned adjacent said containment, whereby zeta potential of an interior surface in fluid contact with the first separation channel can be altered by at least one of:
    a) applying a potential, and
    b) altering at least one of (i) the magnitude, and (ii) polarity, of potential applied, to the distributed source of potential from the power supply.

3. A system as in claim 2, wherein the continuous electric field intensity gradient generator comprises a continuously varying resistor comprising a contour resistor in fluid communication with the first separation channel along at least a portion of the longitudinal axis intermediate the first and second ends, said resistor having a resistance that varies as a continuous function of position along the longitudinal axis of the first separation channel, whereby an electrical potential in the electrolyte fluid varies as a non-linear continuous function of position along the longitudinal axis of the first separation channel and, as a result, the electric field intensity varies as a continuous function of position along the longitudinal axis over at least a portion of the first separation channel intermediate the first and second ends.

4. A system as in claim 3, wherein the continuously varying resistor comprises a filament within the first separation channel.

5. A system as in claim 3, wherein the continuously varying resistor comprises a packing within the first separation channel that varies in resistivity as a continuous function of position along the longitudinal axis.

6. A system as in claim 3, wherein said contour resistor comprises a conductive material having a cross sectional shape which varies as a continuous function of position along the longitudinal axis.

7. A system as in claim 3, wherein said contour resistor has a material property that varies as a continuous function of position along said longitudinal axis.

8. A system as in claim 1, wherein the continuous electric field intensity gradient generator further comprises:
    a cathode positioned adjacent one of the first and second ends of the first separation channel;
    an anode positioned adjacent the other of the first and second ends of the first separation channel;
    a power supply in electric communication with the cathode and the anode;
    a continuously varying resistor in fluid communication with the first separation channel along at least a portion of the longitudinal axis intermediate the first and second ends said resistor having a distance that varies as a continuous function of position along the longitudinal axis of the first separation channel, whereby an electric potential in the electrolyte fluid varies as a non-linear continuous function of position along the longitudinal axis of the first separation channel and, as a result, the electric field intensity varies as a continuous function of position along the longitudinal axis over at least a portion of the first separation channel intermediate the first and second ends.

9. A system as in claim 1, further comprising an electrolyte solution disposed in the first separation channel.

10. A system as in claim 9, wherein the electrolyte solution comprises a buffer solution.

11. A system as in claim 9, further comprising a gel disposed in the first separation channel.

12. A system as in claim 9, further comprising a polymeric solution disposed in the first separation channel.

13. A system as in claim 9, further comprising a micellular dispersion disposed in the first separation channel.

14. A system as in claim 1, wherein the containment is configured to provide a high aspect substantially rectangular cross-sectional shape for the first separation channel.

15. A system as in claim 14, wherein the electroosmotic flow generator comprises a first plate disposed adjacent one side of the containment and configured to alter the zeta potential on an interior surface of the first separation channel adjacent the first side of the containment and a second plate adjacent a second side of the containment configured to alter the zeta potential on an interior surface of the containment adjacent the second side of the containment.

16. A system as in claim 1, further comprising a first orientation electric field generator.

17. A system as in claim 16, wherein the first orientation electric field generator comprises an electroosmotic flow generator further comprising a first plate disposed adjacent one side of the containment and configured to alter the zeta potential on an interior surface of the first separation channel adjacent the first side of the containment and a second plate adjacent a second side of the containment configured to alter the zeta potential on an interior surface of the containment adjacent the second side of the containment, wherein the first plate and the second plate are brought to different potentials so as to create an alignment electric field configured to align bipolar molecules in directions normal to the first and second plates.

18. A system as in claim 16, wherein the orientation electric field oscillates at a selected frequency.

19. A system as in claim 16, further comprising a second orientation electric field generator configured for generating a second orientation electric field acting in a direction normal to the first orientation electric field, wherein the first and second orientation electric fields can be varied to orient bipolar molecules to a selected orientation by cooperation between the first and second orientation alignment electric fields.

20. A system as in claim 1, further comprising a detector configured for detecting analyte species in said first separation channel, said detector being positioned intermediate the first and second ends of said first separation channel.

21. A system as in claim 20, further comprising:
a steering valve in fluid communication with the first separation channel, said steering valve comprising a connecting channel and configured to selectively divert fluid containing analyte species from said first separation channel at a location intermediate the first and second ends of the first separation channel into the connecting channel;

a second separation channel adapted for containing electrolyte fluid and analyte species, said second separation channel having a longitudinal axis and a first end and a second end, said second separation channel being in fluid communication with the connecting channel of said steering valve at a location intermediate said first and second ends, and, an electric field generator configured for moving analyte species along the second separation channel by at least one of electrophoretic migration and electroosmotic flow.

22. A system as in claim 21, further comprising an analyte concentrator located in said second separation channel intermediate the first and second ends.

23. A system as in claim 22, wherein said analyte concentrator comprises a line source of electro potential and an isolated ground, whereby an electric field generated by the second electric field generator can be locally altered so as to focus an analyte species at a location intermediate the first and second ends of the second separation channel.

24. A system as in claim 23, further comprising a first electrode positioned at a first point along the longitudinal axis of the second separation channel, said first electrode being connected to said isolated ground, and a second electrode positioned at a second point along said longitudinal axis of the second separation channel, said second electrode being connected to a source of potential, said source of electro potential being also connected to the isolated ground.

25. The system of claim 24, further comprising an analyte species detector positioned intermediate said first electrode and said second electrode.

26. An electromobility focusing separation system configured to separate analyte species in a fluid sample containing at least one analyte species, comprising:
a first separation channel defined by a containment forming a first elongated separation channel chamber having a longitudinal axis and first end and a second end, said containment configured to contain the fluid sample in the first elongated separation channel chamber, an electrolyte solution contained within the first separation channel an anode adjacent and in fluid communication with the first end of the first elongated separation channel chamber, a cathode adjacent and in fluid communication with the second end of the first elongated separation channel chamber, said containment and said electrolyte solution cooperating to provide a charge accumulation at interior wall surfaces of the first elongated separation channel chamber in response to an applied potential so as to give rise to bulk electroosmotic flow of the electrolyte solution, a first power supply in electric communication with the anode and the cathode and configured to provide an electrical potential there between, whereby electrophoretic migration of analyte species and electroosmotic bulk flow of the electrolyte solution is enabled, a sample injection port coupled to the separation channel, the sample injection port being in fluid communication with the electrolyte solution and enabling injection of a fluid sample containing one or more analyte species into the electrolyte solution, a resistor disposed parallel and in fluid communication with the first elongated separation channel chamber along at least a portion of said first elongated separation channel chamber intermediate the first and second ends thereof, said resistor having a variable resistance varying as a continuous function of position along the longitudinal axis of said first elongated separation channel chamber; and, a first electric field generator configured to control the direction and velocity of the electroosmotic bulk flow of the electrolyte solution;

whereby electrophoretic migration of analyte species is effected by an electric field intensity which varies as a continuous function of position along the longitudinal axis of said first elongated separation channel chamber at locations adjacent the resistor, and electrophoretic migration of analyte species and electroosmotic bulk flow of the electrolyte solution can combine to separate analyte species along the longitudinal axis of the first elongated separation channel.

27. A system as in claim 26, wherein the electroosmotic bulk flow is in a direction opposite to a direction of electrophoretic migration of analyte species of interest.

28. A system as in claim 26, wherein the electric field generator configured to control the direction and velocity of the electroosmotic bulk flow of the electrolyte solution comprises a power supply and a distributed source of potential positioned adjacent said containment on an exterior surface, whereby zeta potential of an interior surface in fluid contact with the first separation channel can be altered by at least one of:

a) applying a potential; and, b) altering at least one of (i) the magnitude, and (ii) polarity, of potential applied to the distributed source of potential from the power supply.

29. A system as in claim 26, wherein said resistor is a contour resistor in fluid communication with the first separation channel along at least a portion of the longitudinal axis intermediate the first and second ends, said resistor having a resistance that varies as a continuous function of position along the longitudinal axis of the first separation channel, whereby an electric potential in the electrolyte fluid varies as a non-linear continuous function of position along the longitudinal axis of the first separation channel, and as a result the electric field intensity varies as a continuous function of position along the longitudinal axis over at least a portion of the first separation channel intermediate the first and second ends.

30. A system as in claim 29, wherein said contour resistor comprises a conductive material having a cross-sectional shape which varies as a continuous function of position along the longitudinal axis.

31. A system as in claim 29, wherein said contour resistor has a material property that varies as a continuous function of position along said longitudinal axis.

32. A system as in claim 26, wherein the resistor is a continuously varying resistor in fluid communication with the first separation channel along at least a portion of the longitudinal axis intermediate the first and second ends, said resistor having a resistance that varies as a continuous function of position along the longitudinal axis of the first separation channel, whereby an electric potential in the electrolyte fluid varies as a non-linear continuous function of position along the longitudinal axis of the first separation channel, and as a result the electric field intensity varies as a continuous function of position along the longitudinal axis over at least a portion of the first separation channel intermediate the first and second ends.

33. A system as in claim 32, wherein the continuously varying resistor comprises a filament within the first separation channel.

34. A system as in claim 32, wherein the continuously varying resistor comprises a packing within the first separation channel that varies in resistivity as a continuous function of position along the longitudinal axis.

35. A system as in claim 26, wherein the electrolyte solution comprises a buffer solution.

36. A system as in claim 26, further comprising a gel disposed in the first separation channel.

37. A system as in claim 26, further comprising a polymeric solution disposed in the first separation channel.

38. A system as in claim 26, further comprising a micellular dispersion disposed in the first separation channel.

39. A system as in claim 26, wherein the containment is configured to provide a high aspect substantially rectangular cross-sectional shape for the first separation channel.

40. A system as in claim 39, wherein the electric field generator configured to control the direction and velocity of the electroosmotic bulk flow of the electrolyte solution comprises a first plate disposed adjacent one side of the containment and configured to alter the zeta potential on an interior surface of the first separation channel adjacent the first side of the containment and a second plate adjacent a second side of the containment configured to alter the zeta potential on an interior surface of the containment adjacent the second side of the containment.

41. A system as in claim 26, further comprising a first orientation electric field generator.

42. A system as in claim 41, wherein the first orientation electric field generator comprises an electroosmotic flow generator further comprising a first plate disposed adjacent one side of the containment and configured to alter the zeta potential on an interior surface of the first separation channel adjacent the first side of the containment, and a second plate adjacent a second side of the containment configured to alter the zeta potential on an interior surface of the containment adjacent the second side of the containment, wherein the first plate and the second plate are brought to different potentials so as to create an alignment electric field configured to align bipolar molecules in directions normal to the first and second plates.

43. A system as in claim 42 wherein the orientation electric field oscillates at a pre-selected frequency.

44. A system as in claim 42, further comprising a second orientation electric field generator configured for generating a second orientation electric field acting in a direction normal to the first orientation electric field, wherein the first and second orientation electric fields can be varied to orient bipolar molecules to a selected orientation by cooperation between the first and second orientation alignment electric fields.

45. A system as in claim 26, further comprising a detector configured for detecting analyte species in said first separation channel, said detector being positioned intermediate the first and second ends of said first separation channel.

46. A system as in claim 45, further comprising:

a steering valve in fluid communication with the first separation channel, said steering valve comprising a connecting channel and configured to selectively divert fluid containing analyte species from said first separation channel at a location intermediate the first and second ends of the first separation channel into the connecting channel;

a second separation channel adapted for containing electrolyte fluid and analyte species, said second separation channel having a longitudinal axis and a first end and a second end, said second separation channel being in fluid communication with the connecting channel of said steering valve at a location intermediate said first and second ends, and, a second electric field generator configured for moving analyte species along the second separation channel by at least one of electrophoretic migration and electroosmotic flow.

47. A system as in claim 46, further comprising an analyte concentrator located in said second separation channel intermediate the first and second ends.

48. A system as in claim 47, wherein said analyte concentrator comprises at least one line source of electropotential and an isolated ground, whereby an electric field generated by the second electric field generator can be locally altered so as to focus an analyte species at a location intermediate the first and second ends of the second separation channel.

49. A system as in claim 48, wherein the line source comprises a first electrode positioned at a first point along the longitudinal axis of the second separation channel, said first electrode being connected to said isolated ground, and the system further comprises a second electrode positioned at a second point along said longitudinal axis of the second separation channel, said second electrode being connected to a source of potential, said source of electro potential being also connected to the isolated ground.

50. The system of claim 49, further comprising an analyte species detector positioned intermediate said first electrode and said second electrode.

51. An electromobility focusing separation system configured to separate analyte species in a fluid sample containing at least one analyte species, comprising:

a first separation channel defined by a containment forming a first elongated separation channel chamber having a longitudinal axis and first end and a second end, said containment configured to contain the fluid sample in the first elongated separation channel chamber, an electrolyte solution contained within the first separation channel, said containment and said electrolyte solution cooperating to provide a charge accumulation at interior wall surfaces of the first elongated separation channel chamber so as to give rise to bulk electroosmotic flow of the electrolyte solution; a first electric field generator:

an anode adjacent and in fluid communication with the first end of the first elongated separation channel chamber; and a cathode a adjacent and in fluid communication with the second end of the first elongated separation channel chamber;

a first power supply in electrical communication with the anode and the cathode and configured to provide an electrical potential there between, whereby electrophoretic migration of analyte species and electroosmotic bulk flow of the electrolyte solution is enabled;

a sample injection port intermediate the first and second ends of the separation channel, the sample injection port being in fluid communication with the electrolyte solution and enabling injection of a fluid sample containing one or more analyte species into the electrolyte solution;

a contour resistor disposed parallel and in fluid communication with the first elongated separation channel chamber along at least a portion of said first elongated separation channel chamber intermediate the first and second ends thereof, said contour resistor having a variable resistance varying as a continuous function of position along the longitudinal axis of said first elongated separation channel chamber; and, a second electric field generator configured to control the direction and velocity of electroosmotic bulk flow of the electrolyte solution, whereby electrophoretic migration of analyte species is effected by an electric field intensity which varies as a continuous function of position along the longitudinal axis of said first elongated separation channel chamber at locations adjacent the contour resistor, and electrophoretic migration of analyte species and electroosmotic bulk flow of the electrolyte solution can combine to separate analyte species along the longitudinal axis of the first elongated separation channel; and a detector configured for detecting analyte species in said first separation channel, said detector being positioned intermediate the first and second ends of said first separation channel.

52. A system as in claim 51, further comprising:

a steering valve in fluid communication with the first separation channel, said steering valve comprising a connecting channel and configured to selectively divert fluid containing analyte species from said first separation channel at a location intermediate the first and second ends of the first separation channel into the connecting channel;

a second separation channel adapted for containing electrolyte fluid and analyte species, said second separation channel having a longitudinal axis and a first end and a second end, said second separation channel being in fluid communication with the connecting channel of said steering valve at a location intermediate said first and second ends, and, a third electric field generator configured for moving analyte species along the second separation channel by at least one of electrophoretic migration and electroosmotic flow.

53. A system as in claim 52, further comprising an analyte concentrator located in said second separation channel intermediate the first and second ends.

54. A system as in claim 53, wherein said analyte concentrator comprises a line source of electric potential and an isolated ground, whereby an electric field generated by the third electric field generator can be locally altered so as to focus an analyte species at a location intermediate the first and second ends of the second separation channel.

55. A system as in claim 54, wherein the line source of electric potential a first electrode positioned at a first point along the longitudinal axis of the second separation channel, said first electrode being connected to said isolated ground, and the system further comprises a second electrode positioned at a second point along said longitudinal axis of the second separation channel, said second electrode being connected to a source of potential, said source of electro potential being also connected to the isolated ground.

56. The system of claim 55, further comprising an analyte species detector positioned intermediate said first electrode and said second electrode.

57. A liquid-phase electromobility focusing separation system configured to separate at least one discrete analyte species from an analyte sample, comprising:

a first separation channel defined by a confinement enclosing an interior channel volume, said first separation channel having first and second ends and a longitudinal axis, and said first separation channel being configured to contain an electrolyte solution within the interior channel volume, said separation channel providing a common flowpath for both the analyte sample and the electrolyte solution;

a continuous electric field intensity gradient generator, further comprising a continuously variable resistor disposed adjacent said separation channel, said continuous electric field intensity gradient generator being configured to apply a electric field intensity gradient within the first separation channel along the longitudinal axis over at least a portion of the first separation channel intermediate the first and second ends, the intensity of electric field generated varying as a continuous function of location along the longitudinal axis, whereby electrophoretic migration of an analyte species within the first separation channel is actuated by a force that varies with position along the longitudinal axis as a continuous function of position along the longitudinal axis within said portion of the first separation channel;

a fluid flow generator configured to generate a fluid flow along the longitudinal axis of the first separation channel, which flow is controllable and is configured to provide a force on the analyte species acting in opposition to the electric field intensity gradient, to enhance separation of said at least one analyte species by enabling separation control of an interaction of forces created by the continuous electric field intensity gradient generator and the fluid flow generator.

58. A system in accordance with claim 57, wherein the fluid flow generator further comprises a pump fluidly connected to the separation channel, said pump being configured to provide a pump-induced fluid flow through the separation channel to provide a counter-balancing hydrodynamic force.

59. An electromobility focusing separation system configured to separate analyte species in a fluid sample containing at least one analyte species, comprising:

a first separation channel defined by a containment forming a first elongated separation channel chamber having a longitudinal axis and first end and a second end, said containment configured to contain the fluid sample in the first elongated separation channel chamber, an electrolyte solution contained within the first separation channel an anode adjacent and in fluid communication with the first end of the first elongated separation channel chamber, a cathode adjacent and in fluid communication with the second end of the first elongated separation channel chamber, a first power supply in electric communication with the anode and the cathode and configured to provide an electrical potential there between, whereby electrophoretic migration of analyte species is enabled, a sample injection port coupled to the separation channel, the sample injection port being in fluid communication with the electrolyte solution and enabling injection of a fluid sample containing one or more analyte species into the electrolyte solution, a resistor disposed parallel and in fluid communication with the first elongated separation channel chamber along at least a portion of said first elongated separation channel chamber intermediate the first and second ends thereof, said resistor having a variable resistance varying as a function of position along the longitudinal axis of said first elongated separation channel chamber; and, a fluid flow generator configured to provide a relative counter bulk flow of the electrolyte solution, whereby electrophoretic migration of analyte species is effected by an electric field intensity which varies as a continuous function of position along the longitudinal axis of said first elongated separation channel chamber at locations adjacent the resistor, and electrophoretic migration of analyte species and bulk flow of the electrolyte solution can combine to separate analyte species along the longitudinal axis of the first elongated separation channel.

60. A system in accordance with claim 59, wherein the fluid bulk flow generator comprises a electric field generator configured to create and control the direction and velocity of an electro-osmotic bulk flow of the electrolyte solution, said containment and said electrolyte solution cooperating to provide a charge accumulation at interior wall surfaces of the first elongated separation channel chamber in response to an applied potential so as to give rise to bulk electro-osmotic flow of the electrolyte solution.

61. A system in accordance with claim 59, wherein the fluid bulk flow generator comprises a pump configured to provide a pump-induced flow providing a counter acting force to the electrophoretic migration of analyte species.

* * * * *